United States Patent [19]
Sawada et al.

[11] Patent Number: 6,160,142
[45] Date of Patent: Dec. 12, 2000

[54] METALLIC SOAP FINE PARTICLES, PROCESS FOR PRODUCING SAME AND USE OF SAME

[75] Inventors: Kouhei Sawada; Shinji Nakamura; Show Onodera, all of Hyogo-ken, Japan

[73] Assignee: NOF Corporation, Tokyo, Japan

[21] Appl. No.: 09/148,323

[22] Filed: Sep. 4, 1998

[30] Foreign Application Priority Data

| Sep. 11, 1997 | [JP] | Japan | 9-247211 |
| Mar. 20, 1998 | [JP] | Japan | 10-072813 |
| Mar. 20, 1998 | [JP] | Japan | 10-072815 |
| Mar. 20, 1998 | [JP] | Japan | 10-072816 |

[51] Int. Cl.$^7$ ................................................. C07C 51/00
[52] U.S. Cl. ............................ 554/158; 554/153; 554/71; 430/110
[58] Field of Search ..................... 554/153, 158, 554/71; 430/110

[56] References Cited

U.S. PATENT DOCUMENTS 2,945,051  7/1960  Davis .
3,111,381  11/1963  Panzer et al. .

FOREIGN PATENT DOCUMENTS

0429692A1  6/1991  European Pat. Off. .
2180948    4/1987  United Kingdom .

OTHER PUBLICATIONS

*Chemical Abstracts*, vol. 103 (1985), 16–12, No. 24, p. 65 (103:197323g).
Abstract of JP 60–67442 (1985)—WPI/Derwent, Section Ch, Week 8524.

*Primary Examiner*—Deborah D. Carr
*Attorney, Agent, or Firm*—Antonelli, Terry, Stout & Kraus, LLP

[57] ABSTRACT

There are disclosed metallic soap fine particles which have an average particle size of 4 μm or smaller and have a content of particles having particle sizes of 10 μm or larger of at most 4% by weight based on the whole metallic soap fine particles; a process for producing the metallic soap fine particles, comprising mixing (a) an aqueous solution containing 0.001 to 20% by weight of an alkali metal salt or an ammonium salt of a fatty acid having 4 to 30 carbon atoms with (b) an aqueous solution or dispersion containing 0.001 to 20% by weight of an inorganic metal salt at a specific temperature to form a slurry of the metallic soap, and drying the resultant slurry at a specific temperature. The metallic soap, which has remarkably fine particles and narrow particle size distribution, is well suited for use e.g. as a toner additive in an electrophotographic copying machine by virtue of the improvements in blocking resistance, fluidity and eliminability of the toner, and also as a cleaning aid in the same owing to the improvement in cleaning performance for residual toner without impairing the surface of a picture image support.

13 Claims, 10 Drawing Sheets

METALLIC SOAP FINE PARTICLES, PROCESS FOR PRODUCING SAME AND USE OF SAME

BACKGROUND OF THE INVENTION

1. Field of the Invention

The present invention relates to metallic soap fine particles. More particularly, it pertains to metallic soap fine particles that are extremely fine and have a narrow particle size distribution, to a process for producing the aforesaid metallic soap fine particles in a simple, easy and efficient manner and to the utilization of the aforesaid metallic soap fine particles as a toner additive and a cleaning aid for use in an image recording apparatus.

2. Description of the Related Arts

Metallic soap has heretofore been widely utilized in a large variety of fields including electronic printing, powder metallurgy, cosmetics, coating materials and resin processing. With the recent progress in a great deal of advanced functionalization in these fields, further fineness or hyperfineness has come to be required of the metallic soap so as to meet the above-mentioned requirement of advanced functionalization.

Typical examples of processes for producing metallic soap that are carried out at the present time, include a process in which a solution of an inorganic metal compound is added dropwise to a solution containing an alkali metal salt of a fatty acid to cause a reaction (double decomposition process) and a process in which a fatty acid is reacted with an inorganic metal compound under kneading at an elevated temperature (fusion process). However, the metallic soap obtained by any of these processes has an average particle size larger than 7 $\mu$m and further has a ratio by weight of particles having a particle size of 10 $\mu$m or larger to the whole particles of the metallic soap being more than 20%. Consequently, when any of these processes is employed, it is impossible to efficiently produce matallic soap having an average particle size of 4 $\mu$m or smaller. There is disclosed a continuous process capable of producing metallic soap fine particles having an average particle size in the range of 5 to 10 $\mu$m (Japanese Patent Application Laid-Open No. 299247/1989(Hei-1). Nevertheless, the abovementioned process is not necessarily satisfactory in order to efficiently produce metallic soap fine particles having an average particle size in the range of 4 $\mu$m or smaller. Under such circumstances, an attempt is made to develop a process capable of producing further fine metallic soap by pulverizing and classifying the aforesaid metallic soap. However, with the present state of the art it is quite difficult to obtain matallic soap having an average particle size of 4 $\mu$m or smaller by means of classification. In addition, when the aforesaid classification method is used, the product yield is reduced as low as 10% or less and besides, it is made difficult to selectively produce the particles having a size of 10 $\mu$m or smaller. Moreover, the repeated pulverization and classification cause destruction of the surface of the metallic soap fine particles. Consequently, such destruction deteriorates the surface smoothness of the metallic soap fine particles and increases the friction coefficient among said particles, thereby lowering the powder fluidity of the metallic soap.

On the other hand, the application fields utilizing such metallic soap fine particles are exemplified by toner particles and a cleaning aid in an electrophotographic copying machine.

A variety of methods for use in electrophotographic copying machines are known as described in U.S. Pat. No. 2,297,691 and Japanese Patent Publication Nos. 23910/1967 (Sho-42) and 24748/1968 (Sho-43). In general, the foregoing methods comprise the steps of forming an electric latent image on a picture image support by any of various methods through the utilization of a photoconductive material; developing said electric latent image by the use of a toner; and at need transferring and fixing said image on a recording medium such as a sheet of paper or a polymer to obtain a sensible picture image. The picture image support after the transfer is used repeatedly, after the toner remaining on the surface thereof has been removed. A variety of methods have heretofore been proposed as a development method by using a toner, such as a method for fixing a toner image and a method for cleaning the toner remaining on a picture image support. The method suited to the respective image forming process is adopted from the variety of methods.

There have heretofore been proposed, as a process for producing a toner to be used for these purposes, a process for producing toner fine particles in which a colorant such as a dyestuff or pigment is melt mixed with a thermoplastic resin in general and is uniformly dispersed therein, and the resultant uniform mixture is turned into toner fine particles having a desired particle size by the use of a pulverizing apparatus and a classifying machine as disclosed in Japanese Patent Application Laid-Open No. 276764/1992 (Hei -4) and a process for producing toner fine particles by uniformly dissolving or dispersing a polymerizable monomer, a colorant and a polymerization initiator, and as necessary, a crosslinking agent and/or a charge contolling agent, and thereafer turning the resultant monomer composition into toner fine particles by means of suspension polymerization method as described in Japanese Patent Publication Nos. 10231/1961 (Sho-36) 10799/1968 (Sho-43) and 14895/1976 (Sho-51).

The toner produced by any of these procsses is usually used in an electronic copying apparatus, an electrostatic printer and the like. Moreover, the high densification and colorfulness of printing in recent years have come to call for improvement in preservation stability of toner particles; for enhancement in the speed and precision of visible image formation of a toner for a picture image support; for enhancement in the speed and precision of transfer of an visible image from a picture image support to a recording medium; for enhancement in the speed and precision of fixing the visible image; and also for enhancement in the speed and precision of cleaning for the toner remaining on the picture image support. Accordingly, advanced characteristics higher than anything before have required of a toner for use in an electronic copying apparatus and of an additive for use in a cleaning aid.

It has hitherto been known that improvements can be made in blocking resistance of a toner, in fluidity thereof, in eliminability from an toner image support or in cleaning properties by adding metallic soap such as zinc stearate or calcium stearate to a toner or a cleaning aid. For example, the cleaning performance for a picture image support is improved by adding metallic soap as a cleaning aid to a toner as disclosed in Japanese Patent Application Laid-Open Nos. 111576/1982 (Sho-57), 225870/1985 (Sho-60), 106780/1990 (Hei-2) and 269478/1991 (Hei-3). Further there is known a cleaning method for a picture image support using a cleaning brush or a blade which has previously been used, in which method the surface of the picture image support is coated with metallic soap of a saturated fatty acid or metallic soap of an unsaturated fatty acid as a cleaning aid, as disclosed in Japanese Patent Application Laid-Open No. 73774/1982 (Sho-57). The above-mentioned cleaning method makes it possible to alleviate the friction on the picture image support due to a cleaning brush or a blade by said coating and at the same time, makes it possible to facilitate the eliminability of foreign matters stuck to the picture image support.

However, metallic soap containing large-size particles, when added to said toner fine particles internally or b externally, fails to sufficiently be dispersed in said toner fine particles. In addition, the metallic soap containing large-size particles exerts such evil influences on the toner and image support, etc. as described in the following: The reproducibility of the toner fluidity is lowered, and the accuracy or precision of the visible image formation is made insufficient; the service life of the image support is shortened by the abrasion or frictional damage due to the large-size particles contained in the metallic soap at the time of forming visible image of the toner on the the image support; the service life of the image support is shortened by the abrasion or frictional damage due to the large-size particles contained in the metallic soap at the time when the image support is coated with metallic soap as a cleaning aid which has conventionally been used; and accordingly, sufficient image density is made impossible to obtain during a long-term running and besides, a vivid image is made difficult to obtain over a long period of time.

On the other hand, the fields utilizing such metallic soap fine particles are exemplified by the fields of powder metallurgy, cosmetics, coating materials and resin processing, respectively in addition to the above-mentioned field of an electronic printing.

The metallic soap is generally used as a fluidity improver for metallic powders in the field of powder metallurgy. In recent years, further particle size reduction for metallic powders and fineness of a firing mold have been progressing in the field of powder metallurgy. However, the conventional metallic soap, when used for said purpose of use, fails to be sufficiently uniformly dispersed in metallic powders, since said metallic soap powders have large particle sizes as compared with those of the metallic powders, and also have a high content of particles larger than 10 $\mu$m. As a result, unfavorable problems take place in that the fluidity of metallic powders in a mold becomes insufficient and in particular, the strength of filaments as well as production efficiency are lowered in the case where fine metal processing such as filament processing is required.

Moreover, metallic soap is generally used as a pigment dispersant in the field of coating materials. Accompanying further film-thinning in recent years, it is desired in this field that improvements be made in the smoothness of coating surfaces, in sliding property of coating surfaces and in water repellency of film and coating. However, conventional metallic soap, when added to a coating material, brings about such hindrances and troubles as described hereunder: it is made difficult thereby to obtain a coating in which the metallic soap is uniformly dispersed by reason of insufficient dispersibility of the metallic soap in the coating material; sliding property and water repellency to be imparted to the coating by the metallic soap are made insufficient thereby; and besides the surface smoothness of the coating is impaired by the adverse influence of the large-size particles of the metallic soap in the case of forming a coating having a thickness of 10 g m or smaller.

Moreover, metallic soap is generally used as a stabilizing agent and processing aid in the field of resin processing. However, conventional metallic soap, when added to a resin at the time of its processing, gives rise to the following hindrances and troubles as pointed out in said field: The resin processing takes an unreasonably long hours by reason of insufficient dispersibility thereof in resin powders and the like; and the processed resin suffers from white turbidity and decreases in strength and product yield because of insufficient dispersibility of the metallic soap in the processed resin product.

It is forced to say by the troubles and disadvantages as described hereinbefore that the application of the conventionally used metallic soap to the foregoing fields causes extreme difficulty. Such being the case, it has eagerly been desired in the foregoing fields to develop novel metallic soap which has an average particle size markedly smaller than that of the conventionally used metallic soap and which is minimized in the content of large-size particles, more specifically novel metallic soap hyperfine particles which has an average particle size of 4 $\mu$m or smaller and which is minimized in the content of particles having sizes of 10 $\mu$m or larger. It is extremely difficult, however, to efficiently produce metallic soap fine particles by the use of the conventional processes for producing, pulverizing and classifying the conventional metallic soap. Thus it has hitherto been desired to develop a practical production process for efficiently producing the metallic soap having hyperfine particles. In order to produce the same to be used for the foregoing purposes, it is ideal to develop a process capable of containing, as much as possible, metallic soap fine particles having particle sizes of 4 $\mu$m or smaller upon the completion of the synthesis by dispensing to the utmost with a pulverizing step for the synthesized product.

SUMMARY OF THE INVENTION

Under such circumstances, a general object of the invention is to provide metallic soap fine particles which have an average particle size markedly smaller than that of the conventionally used metallic soap, which have narrow particle size distribution, and which are minimized in the content of large-size particles.

Another object of the invention is to provide a process for producing metallic soap fine particles in a simple, easy and efficient manner.

Still another object of the invention is to improve the problems caused in a variety of the application fields as described hereinbefore.

In order to achieve the foregoing objects, intensive research and investigation were accumulated by the present inventors. As a result, there have been found metallic soap fine particles which have an average particle size of 4 $\mu$m or smaller, and which have narrow particle size distribution, and at the same time a process for producing said metallic soap fine particles in a simple, easy and efficient manner which process comprises the steps of mixing at a specific temperature, an aqueous solution of a fatty acid salt at a prescribed concentration with an aqueous solution or dispersion of an inorganic metal salt at a prescribed concentration to form a slurry of metallic soap, and drying the resultant slurry at a specific temperature. There have also been found; that the several problems caused in said various fields can be improved by the use of the metallic soap fine particles produced in accordance with the invention; that improvements can be made in blocking resistance of a toner, in fluidity thereof, in eliminability from a toner image support and in cleaning performances of the toner stuck to the toner image support, and a sufficiently visible image can be formed on the toner image support without impairing the surface of the image support in an electrophotographic copying machine; that improvements can be made in eliminability from a toner image support and in cleaning performances of the toner remaining on the surface of the toner image support after the transferring of the toner from the surface of the toner image support to a recording medium without impairing the surface of the image support in an electrophotographic copying machine, by coating the surface of the image support with a cleaning aid comprising the metallic soap according to the present invention. The present invention has been accomplished on the basis of the findings and information concerned with the foregoing whole items.

Specifically, the present invention provides metallic soap fine particles comprising fine particles which have an average particle size of 4 μm or smaller and which have a content of particles having particle sizes of 10 μm or larger of at most 4% by weight based on the whole particles of the metallic soap. Preferably, the metallic soap fine particles have a difference in particle size ($R_C$–$R_A$) of at most 3 μm between the particle size showing 70% ($R_C$) in a cumulative particle size distribution curve for said metallic soap fine particles and the particle size showing 30% ($R_A$) in the same, and/or preferably, the metallic soap fine particles have a difference in particle size ($R_D$–$R_B$) of at most 6 μm between the particle size showing 95% ($R_D$) in a cumulative particle size distribution curve for said metallic soap fine particles and the particle size showing 50% ($R_S$) in the same.

The present invention further provides a process for producing metallic soap fine particles in a simple, easy and efficient manner which comprises the steps of mixing (a) an aqueous solution containing 0.001 to 20% by weight of an alkali metal salt or an ammonium salt of a fatty acid having 4 to 30 carbon atoms with (b) an aqueous solution or dispersion containing 0.001 to 20% by weight of an inorganic metal salt at a temperature not higher than the starting temperature for crystal transition of the metallic soap to be produced to form a slurry of metallic soap, and drying treating the resultant slurry at a temperature not higher than the starting temperature for crystal transition of the metallic soap to be produced.

The present invention still further provides, as application examples of the metallic soap fine particles, a toner composition for an eletrophotographic copying machine comprising said metallic soap fine particles, especially fine particles of a metallic salt of a fatty acid, and a cleaning aid for an image recording apparatus comprising said metallic soap fine particles, especially fine particles of a metallic salt of a fatty acid.

DESCRIPTION OF THE PREFERRED EMBODIMENTS

Figure 1:
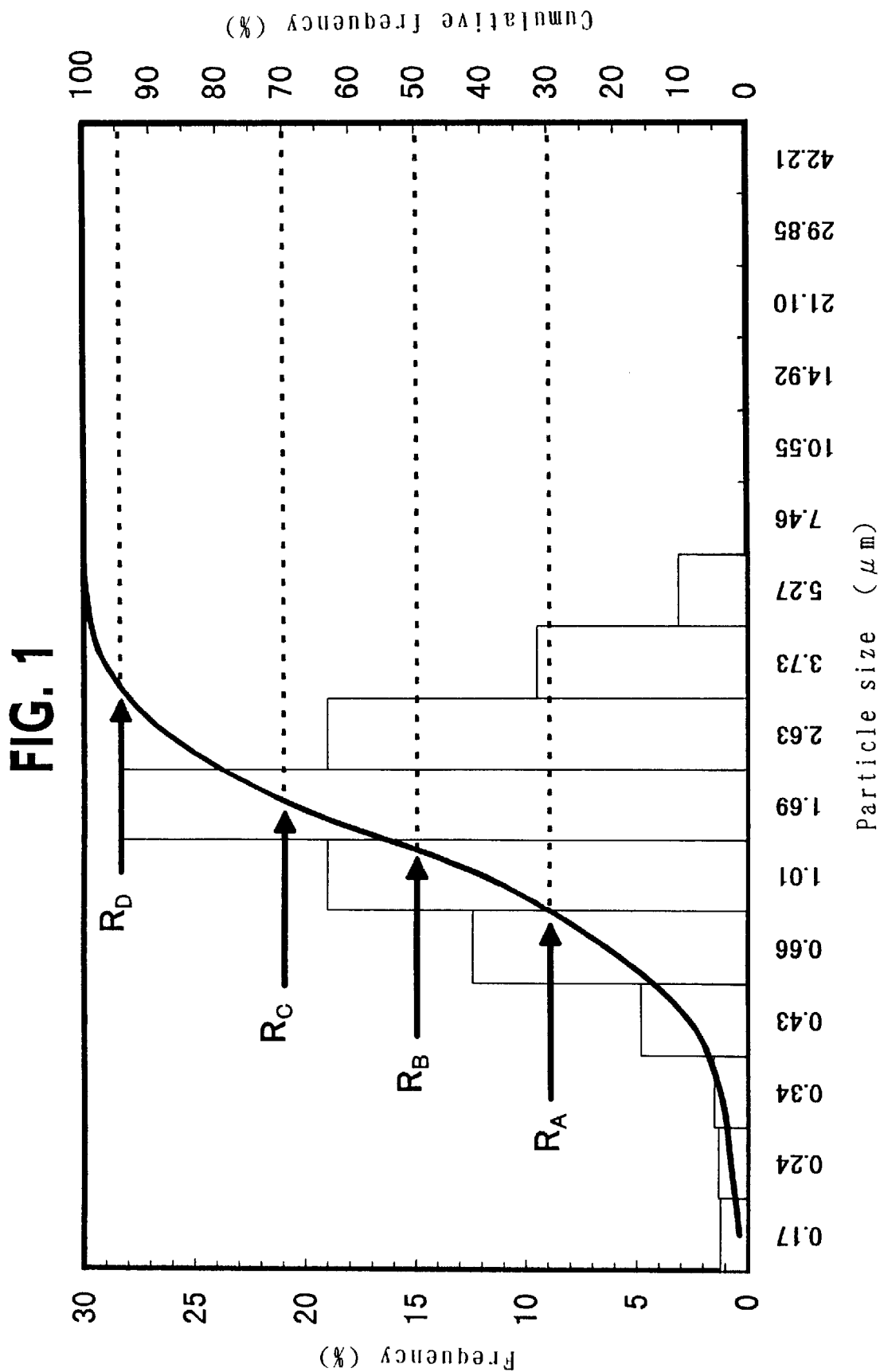
FIG. 1 is a graph showing particle size distribution and cumulative particle size distribution of metallic soap (zinc stearate) of the present invention.

The metallic soap according to the present invention is characterized in that said metallic soap fine particles comprises fine particles which have an average particle size of 4 μm or smaller and which have a content of particles having particle sizes of 10 μm or larger of at most 4% by weight based on the whole particles of the metallic soap. The particle size distribution curve of the metallic soap may be any arbitrary shape, provided that the aforesaid requirements are met. Examples of the particle size distribution curve include the shape in accordance with a statistical curve such as a binominal distribution curve, a normal distribution curve and a Pearson base frequency distribution curve, and a complex particle size distribution curve wherein at least two statistical curves selected from the foregoing curves are complexed with one another.

The metallic soap to be produced according to the present invention is constituted of a saturated fatty acid or an unsaturated fatty acid each having at least 4 carbon atoms which is typified by fatty acids originating from animal or vegetable oil and fat such as a fractionated fatty acid, fatty acids from beef tallow, fatty acids from soybean oil, fatty acids from coconut oil and fatty acids from palm oil; and a metal such as an alkaline earth metal including calcium, barium and magnesium, titanium, copper, manganese, cadmium, mercury, zirconium, lead, iron, aluminum, cobalt, nickel and silver. The aforesaid fractionated fatty acid is specifically exemplified by caprylic acid, capric acid, lauric acid, myristic acid, myristoleic acid, palmitic acid, isopalmitic acid, palmitoleic acid, stearic acid, behenic acid, lignoceric acid, cerotic acid, montanic acid, isostearic acid, oleic acid, arachinic acid, ricinoleic acid, linolenic acid, behenolic acid and erucic acid. Preferable examples of the metallic soap include any of a Ca salt, Zn salt and Ba salt of any of a saturated fatty acid and an unsaturated fatty acid each having 10 to 24, preferably 12 to 22 carbon atoms. The matallic soap may be used alone or as a mixture of at least two species. In the case of the metallic soap being used in a toner for an electronic copying machine, the metallic soap is preferably a Ca salt, Zn salt or Ba salt of any of a saturated fatty acid and an unsaturated fatty acid each having 14 to 22 carbon atoms, and the matallic soap may be used alone or as a mixture of at least two species. In the case where the metallic soap constituted of a fatty acid having 3 or less carbon atoms is used, there is a fear of bringing about such trouble or disadvantage as insufficiency in lubricity of itself, blocking resistance of a toner, fluidity of a toner and eliminability of a residual toner from an image support at the time of cleaning. On the other hand, in the case of the metallic soap being used as a cleaning aid for an electronic copying machine, the metallic soap is preferably a Ca salt, Zn salt or Ba salt of any of a saturated fatty acid and an unsaturated fatty acid each having 14 to 22 carbon atoms, and the matallic soap may be used alone or as a mixture of at least two species. In the case where the metallic soap constituted of a fatty acid having 3 or less carbon atoms is used, there is a fear of bringing about such trouble or disadvantage as insufficiency in eliminability of a toner from the surface of an image support, that is, insufficiency in cleaning performance for the image support. In the application fields other than the foregoing, the objective effect and advantage can be assured by properly selectively employing one or two or more types of metallic soap in accordance with chemical composition of a solvent and polymer components in a coating material; the type and polymerization degree of resin components to be used for resin processing; the type, particle shape and particle size distribution of a metal to be used at the time of powdery metal working; the contained components and production conditions for use in cosmetics; and the like.

The particle size of the metallic soap as mentioned in the present invention, is defined as the average typical length of the metallic soap, to which is applicable a generally known definition. Examples of the average typical length of the metallic soap include biaxial average diameter, teraxial average diameter (arithmetic average diameter), harmonic average diameter, surface-area average diameter, cubic average diameter, circumscribed rectangle equivalent diameter (Breinygell diameter), square equivalent diameter (Goodman diameter, Berrot/Kenny diameter), circle equivalent diameter(Heywood diameter), rectangular parallelopiped equivalent diameter (geometrical average diameter), cylinder equivalent diameter (Asano diameter), cube equivalent diameter (Andreasen-diameter), sphere equivalent diameter (Wandel diameter), unidirectional diameter (Green diameter, Feret diameter), unidirection divisional diameter (Gebelein diameter), Nassenstein diameter and Stokes diameter. In the present invention, general methods for measuring particle size distribution are used for measuring particle size as defined hereinbefore. Examples of measuring methods include sedimentation method based on Stokes' law (gas-phase sedimentation method, liquid-phase sedimentation method, light transmission method), microscopic method, light scattering method and laser diffraction scattering method. Of these, light scattering method, laser diffraction scattering method and the like are preferably usable, which enable precise measurement for further fine particles in the measuring method as described in the present invention.

The average particle size of the metallic soap fine particles in the present invention, is 4 $\mu$m or smaller, preferably 3 $\mu$m or smaller, more preferably 0,5 to 2.5 $\mu$m, particularly preferably 2 $\mu$m or smaller. The metallic soap having the above-mentioned average particle size is advantageous in use for the aforesaid purposes. The use of metallic soap having an average particle size larger than 4 $\mu$m will cause such disadvantages and troubles as described hereunder: Relatively large particle sizes of said metallic soap as compared with the fine-grained metallic powders, make it impossible to sufficiently disperse said metallic soap in the fine-grained metallic powders and accordingly bring about insufficient fluidity of metallic powders and a decrease in the yield of metallic products; said metallic soap, when used as an additive at the time of resin processing, fails to shorten the resin processing hour, and causes white turbidity on a resin molding; said metallic soap, when added to a coating material to form a coating film of 3 $\mu$m or smaller in thickness, impairs the surface smoothness; said metallic soap, when used in a fine-grained sphericalized toner, impairs the surface of a picture image support in an electrophotographic copying machine, and contaminates the texture of a printed matter, thereby making it impossible to obtain a sufficient image density during a long-term running of an electrophotographic copying machine, moreover insufficient adhesiveness of said metallic soap to the toner surface causes insufficiency in blocking resistance of the toner, fluidity of the toner particles and eliminability of the residual toner from a picture image support at the time of cleaning; and said metallic soap, when used as a cleaning aid in an electrophotographic copying machine wherein fine-grained sphericalized toner is used, impairs the surface of a picture image support in the electrophotographic copying machine, thus failing to improve the cleaning performance of the toner from the surface of the picture image support.

The metallic soap according to the invention has a content of metallic soap fine particles having a particle size larger than 10 $\mu$m of at most 4% by weight based on the entire metallic soap fine particles. Preferably the metallic soap is substantially free from particles having a particle size larger than 10 $\mu$m. It is preferable to employ the metallic soap fine particles satisfying the foregoing requirements when used for the aforesaid application fields.

Particularly preferable metallic soap is that which has an average particle size in the range of 0.5 to 2.5 $\mu$m, which has a content of particles having a particle size larger than 6 $\mu$m of at most 5% by weight based on the entire particles, and which is substantially free from particles having a particle size larger than 10 $\mu$m.

By the term "an average particle size of fine particles" as used herein is meant the average particle size of fine particles that is measured at the point of time when the metallic soap fine particles are produced, in other word, that is measured as such or after drying at need prior to or without the subsequent pulverization or classification. Therefore, the metallic soap fine particles of the present invention are characterized by the absence of rupture cross-section due to pulverization.

The metallic soap, when added to a toner having a particle size of 3 to 5 $\mu$m for an electronic printer, is preferably substantially free from particles having a particle size larger than 10 $\mu$m. The metallic soap which has a content of particles having a particle size larger than 10 $\mu$m being 4% or more by weight based on the entire metallic soap fine particles, when used in a fine-grained sphericalized toner, impairs the surface of a picture image support in an electrophotographic copying machine, and contaminates the texture of a printed matter, thereby making it impossible to obtain a sufficient image density during a long-term running of an electrophotographic copying machine. Moreover insufficient adhesiveness of said metallic soap to the toner surface gives rise to insufficiency in blocking resistance of the toner, fluidity of the toner particles and eliminability of the residual toner from a picture image support at the time of cleaning.

In addition, the metallic soap, when used as a cleaning aid in an electronic copying machine, is preferably substantially free from particles having a particle size larger than 10 $\mu$m. The metallic soap which has a content of particles having a particle size larger than 10 $\mu$m being 4% or more by weight based on the entire metallic soap fine particles, when used as a cleaning aid in an electronic copying machine wherein fine-grained sphericalized toner is used, impairs the surface of a picture image support in the electronic copying machine, thus failing to improve the cleaning performance of the toner from the surface of the picture image support.

Moreover, said metallic soap, when applied to a coating material to form a coating film of 5 $\mu$m or smaller in thickness or used as an additive at the time of resin processing, will cause such disadvantage as impairment to the surface smoothness, insufficient fluidity of the matallic powder, a decrease in the yield of the metal product, insufficient shortening of the resin processing hour and white turbidity of resin moldings.

Figure 2:
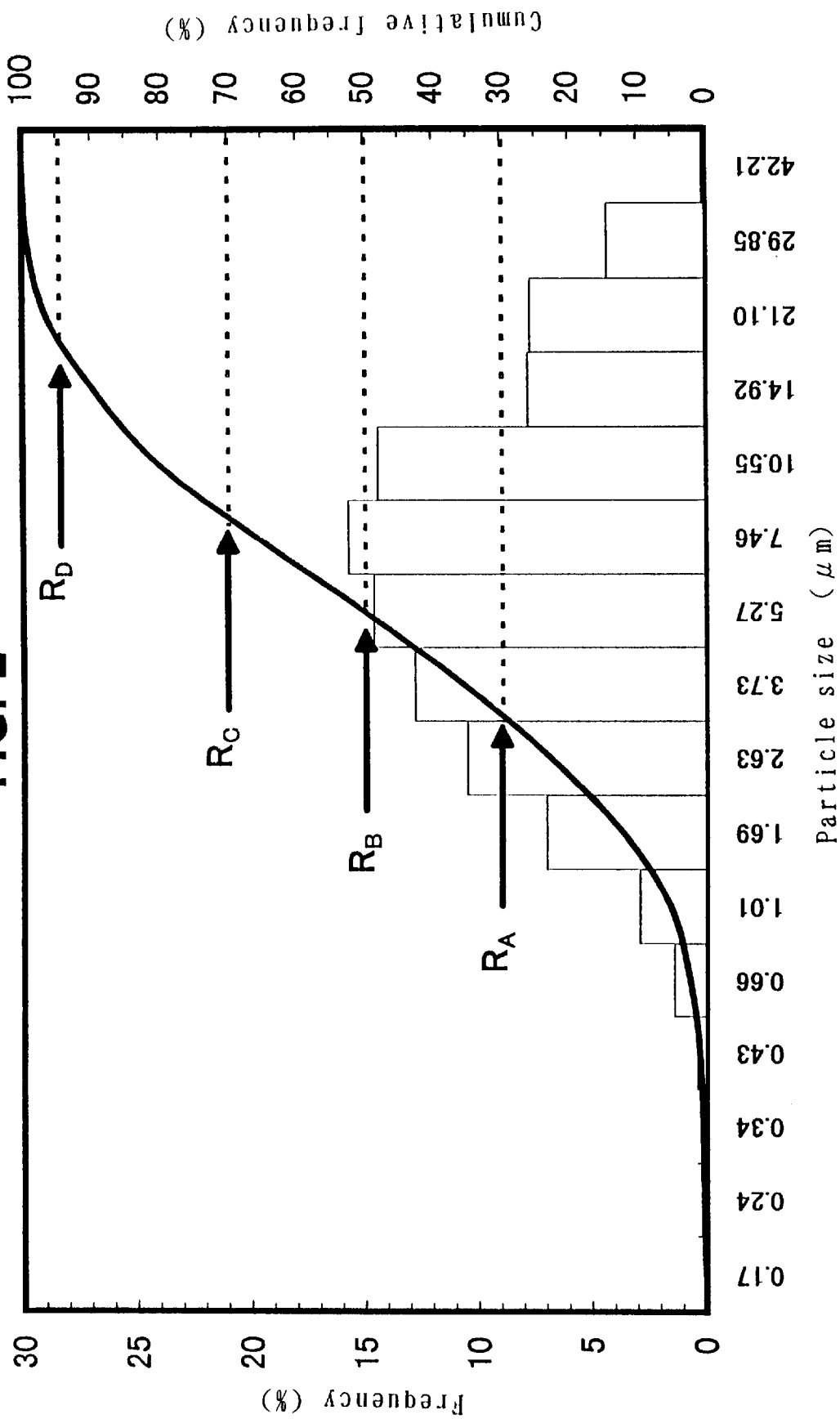
FIG. 2 is a graph showing particle size distribution and cumulative particle size distribution of conventional metallic soap (zinc stearate FIG. 3 is a heat absorption graph through differential thermal analysis to obtain starting temperature for crystal transition of zinc stearate, FIG. 4 is a heat absorption graph through differential thermal analysis to obtain starting temperature for crystal transition of calcium stearate, FIG. 5 is a heat absorption graph through differential thermal analysis to obtain starting temperature for crystal transition of magnesium stearate, FIG. 6 is a schematic constitutional view showing an example of a picture image forming apparatus to which the cleaning aid according to the present invention is applied, FIG. 7 is a scanning electron micrograph (SEM) at a magnification of 2000 (2000×) of the metallic soap prepared in Example 3 of the present invention, FIG. 8 is a SEM at 5000× of the metallic soap prepared in Example 3 of the present invention, FIG. 9 is a SEM at 15000× of the metallic soap prepared in Example 3 of the present invention, and FIG. 10 is a SEM at 2000× of the metallic soap prepared in Comparative Example 4 of the present specification.

Preferably, the matallic soap of the present invention has a value ($R_C$–$R_A$) of at most 3 μm and/or a value of ($R_D$–$R_A$) of at most 6 μm, wherein $R_A$, $R_B$, $R_C$ and $R_D$ are 30%, 50%, 70% and 95% particle size, respectively; 30% particle size $R_A$ (μm) means that particles having the size in question and smaller occupies 30% by weight based on the total weight of the matallic soap fine particles; for example, referring to FIGS. 1 & 2 showing the cumulative particle size distribution graphs of metallic soap (zinc stearate) for the present invention and for conventional use, respectively, 30% particle size by cumualtive weight is designated as $R_A$ (μm); and $R_B$, $R_C$ and $R_D$ are designated in the same manner as above. In FIG. 2, $R_A$, $R_D$, $R_C$ and $R_D$ are 3.2 μm, 5.3 μm, 8.3 μm and 19.6 μm, respectively, and $R^C$–$R_A$ and $R_D$–$R_D$ are 5.1 μm and 14.3 μm, respectively. Thus the scope of the particle size distribution is made narrow with a decrease in the values of $R_C$–$R_A$ and/or $R_D$–$R_D$.

In the metallic soap of the present invention, $R_C$–$R_A$ is at most 3 μm, and $R_D$–$R_B$ is at most 6 μm. In the case of the metallic soap being used in the foregoing application field, $R^C$–$R_A$ is preferably at most 2 μm, more preferably 0.3 to 2 μm, and $R_D$–$R_B$ is preferably 1.5 to 6 μm, more preferably at most 3 μm.

The use of the metallic soap having $R_C$–$R_A$ larger than 3 μm or $R_D$–$R_B$ larger than 6 μm in said application field, for example, in a fine-grained sphericalized toner for an electronic copying machine, will impair the surface of a picture image support in an electrophotographic copying machine and contaminate the surfaces of printed matters during a long-term running of an electrophotographic copying machine, thus disabling to obtain a sufficient image density because of wide particle size distribution of the metallic soap and an increase in the amount of large-sized particles.

Further, the use of said metallic soap in said field will bring about insufficiency in blocking resistance and fluidity of the toner and in the eliminability of the residual toner from the image support at the time of cleaning because of non-uniform adhesion of the metallic soap to the surface of the toner particles.

In addition, the use of the metallic soap having $R_C$–$R_A$ larger than 3 μm or $R_D$–$R_B$ larger than 6 μm as a cleaning aid in an electronic copying machine in which a fine-grained sphericalized toner is used therefor, will impair the surface of an image support in an electronic copying machine and fail to improve the cleaning performance for the toner from the surface of the image support, by reason of the wide particle size distribution of the metallic soap and an increase in the amount of large-sized particles.

Moreover, the use of the metallic soap having $R_C$–$R_A$ larger than 3 μm or $R_D$–$R_B$ larger than 6 μm in the other application fields, for example, in a coating material to form a coating film having a thickness of 5 μm or smaller by adding said metallic soap thereto, will give rise to such disadvantages as impairment to the smoothness of the coating surface, insufficiency in the fluidity of the metallic powders, a decrease in the yield of worked metal product, failure to shorten the resin processing hour and white turbidity on resin moldings.

In the following, detailed description will be given of the suitable process for producing the metallic soap according to the present invention.

There are employed in the production process according to the present invention, (a) an aqueous solution of a fatty acid salt and (b) an aqueous solution or dispersion of an inorganic metal salt.

The fatty acid salt to be used for the preparation of the aqueous solution of a fatty acid salt as the component (a) is exemplified by an alkali metal salt or an ammonium salt of a fatty acid having 4 to 30 carbon atoms. The aforesaid fatty acid may be saturated or unsaturated, and may be straight chain or branched. Examples of such fatty acid salt include an alkali metal salt such as a sodium salt and a potassium salt or an ammonium salt each of a fractionated fatty acid; and an alkali metal salt such as a sodium salt and a potassium salt or an ammonium salt each of fatty acids originating from animal or vegetable oils and fats such as fatty acids from beef tallow, fatty acids from soyean oil, fatty acids from coconut oil and fatty acids from palm oil.

Specific examples of the aforesaid fractionated fatty acid include caprylic acid, capric acid, lauric acid, myristic acid, myristoleic acid, palmitic acid, isopalmitic acid, palmitoleic acid, stearic acid, behenic acid, lignoceric acid, cerotic acid, montanic acid, isostearic acid, oleic acid, arachinic acid, ricinoleic acid, linoleic acid, behenolic acid and erucic acid. Preferable examples of fatty acid salts among them include an alkali metal salt or an ammonium salt each of a fatty acid having 12 to 22 carbon atoms. Any of the fatty acid salts may be used alone or in combination with at least one other species. An alkali metal salt or an ammonium salt each of a fatty acid having 3 or less carbon atoms, when used to form a fatty acid salt, leads to a decrease in the yield of the objective metallic soap because of a high solubility of said metallic soap in water, whereas the use of an alkali metal salt or an ammonium salt each of a fatty acid having 31 or more carbon atoms, causes a decrease in the productivity of the objective metallic soap because of an unreasonably low solubility of said metallic soap in water accompanied by lowered concentration of the aqueous solution thereof.

The content of the alkali metal salt or an ammonium salt each of a fatty acid in the aqueous solution of fatty acid salt as the component (a) in the present invention, is selected in the range of 0.001 to 20% by weight. The content thereof, when being lower than 0.001% by weight, is not realistic because of a low production efficiency due to remarkably lowered concentration of the objective metallic soap in a reaction liquid. On the other hand, The content thereof, when being higher than 20% by weight, brings about a fear of unfavorably enlarging the average particle size of the objective metallic soap. In view of the amount and the particle size of the metallic soap to be obtained, the content of the alkali metal salt or an ammonium salt each of a fatty acid in the aqueous solution of fatty acid salt is preferably in the range of 0.5 to 15% by weight.

Examples of the inorganic metal salt to be used for the preparation of an aqueous solution or dispersion of an inorganic metal salt as the component (b) include a chloride, sulfate, carbonate, nitrate or phosphate each of an alkaline earth metal such as calcium, barium and magnesium, and a chloride, sulfate, carbonate, nitrate or phosphate each of a metal such as titanium, zinc, copper, manganese, cadmium, mercury, zirconium, lead, iron, aluminum, cobalt, nickel and silver. The aforesaid substances may be used alone or in combination with at least one other species.

The content of the inorganic metal salt in the aqueous solution or dispersion of an inorganic metal salt as the component(b) in the present invention, is selected in the range of 0.001 to 20% by weight. The content thereof, when being lower than 0.001% by weight, is not practical because of a low production efficiency due to remarkably lowered concentration of the objective metallic soap in a reaction liquid. On the other hand, The content thereof, when being higher than 20% by weight, brings about a fear of unfavorably enlarging the average particle size of the objective metallic soap. In view of the amount and the particle size of the metallic soap to be obtained, the content of the inorganic metal salt in the aqueous solution or dispersion of an inorganic metal salt is preferably in the range of 0.01 to 10% by weight.

The water to be used for the preparation of the above-mentioned components (a) and (b) may be any of generally used water without specific limitation, but is preferably the water minimized in impurities, which is exemplified by ion-exchange water, purified water and distilled water.

The blending ratio of the above-mentioned components (a) and (b) may be suitably selected without specific limitation, and it is advantageous to select so that the equivalent ratio of the fatty acid salt in the component(a) to the inorganic metal salt in the components(b) becomes in the range of 0.9 to 1.1. When the equivalent ratio thereof departs from said range, a large amount of unreacted starting materials remain, thus necessitating a removal step thereof. In order to minimize the residual impurities, the equivalent ratio thereof is preferably in the range of 0.95 to 1.05.

The production equipment in the process according to the present invention is preferably capable of separately feeding the component (a) and the components (b) in a mixer, and mixing the same therein. It is advantageous, for example, to feed each of the solutions or dispersions of the starting materials into a mixing tank in different directions from each other to mix the same, and simultaneously with the mixing to discharge the resultant mixture to the outside of reaction system.

The equipment to be used for the operation is preferably capable of uniformly and efficiently mixing both the components(a) and (b). Preferable examples of the equipment include a line mill such as a flow jet mixer, a line homogenizer and a sand mill. In the case where an alkali metal salt or an ammonium salt of an unreacted fatty acid remains after the reaction of the components(a) and (b) said alkali metal salt or an ammonium salt of an unreacted fatty acid can be reacted into metallic soap by mixing the solution or dispersion containing 0.001 to 15% by weight of an inorganic metal salt after the discharge of the components (a) and (b).

Figure 3:
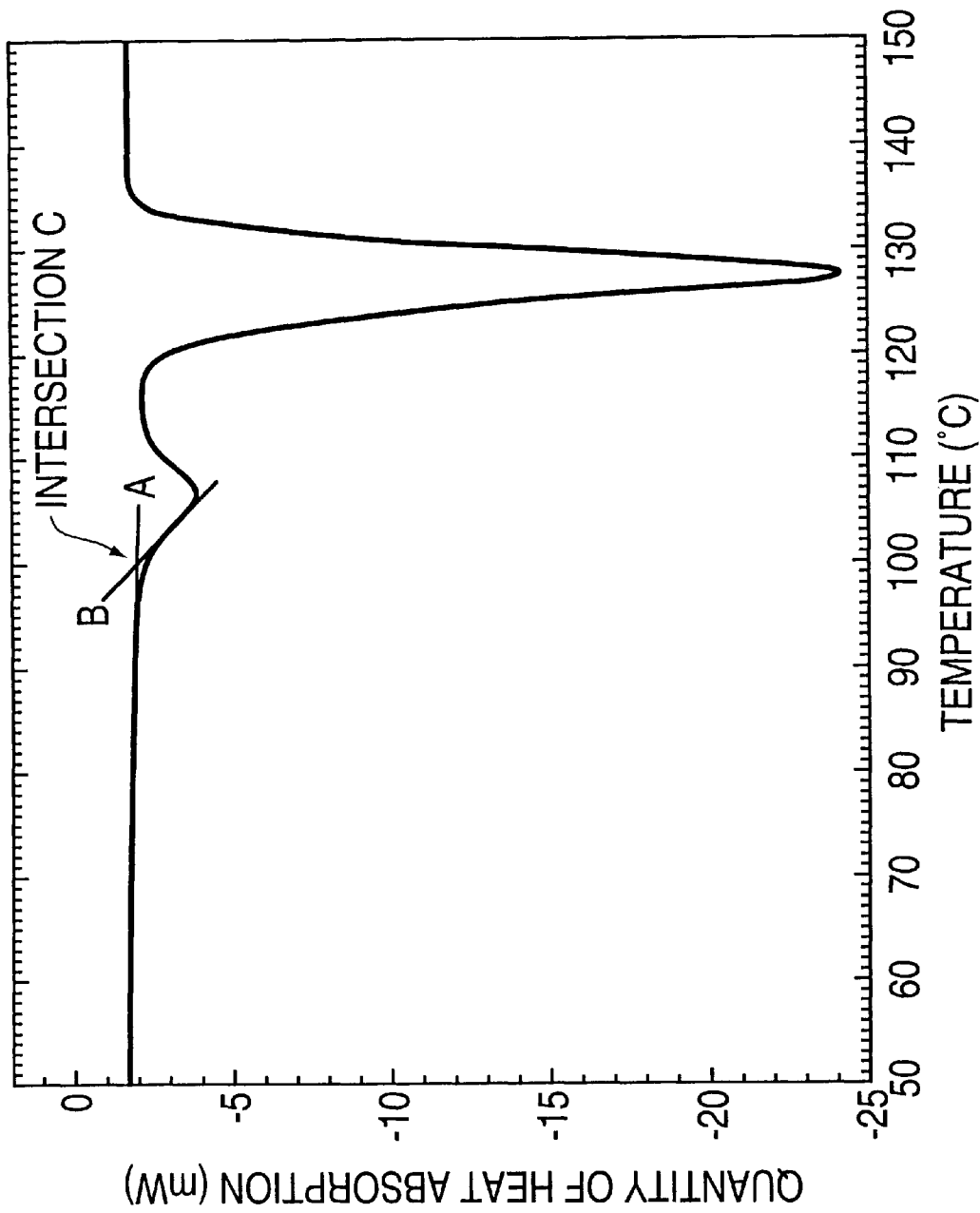
Figure 4:
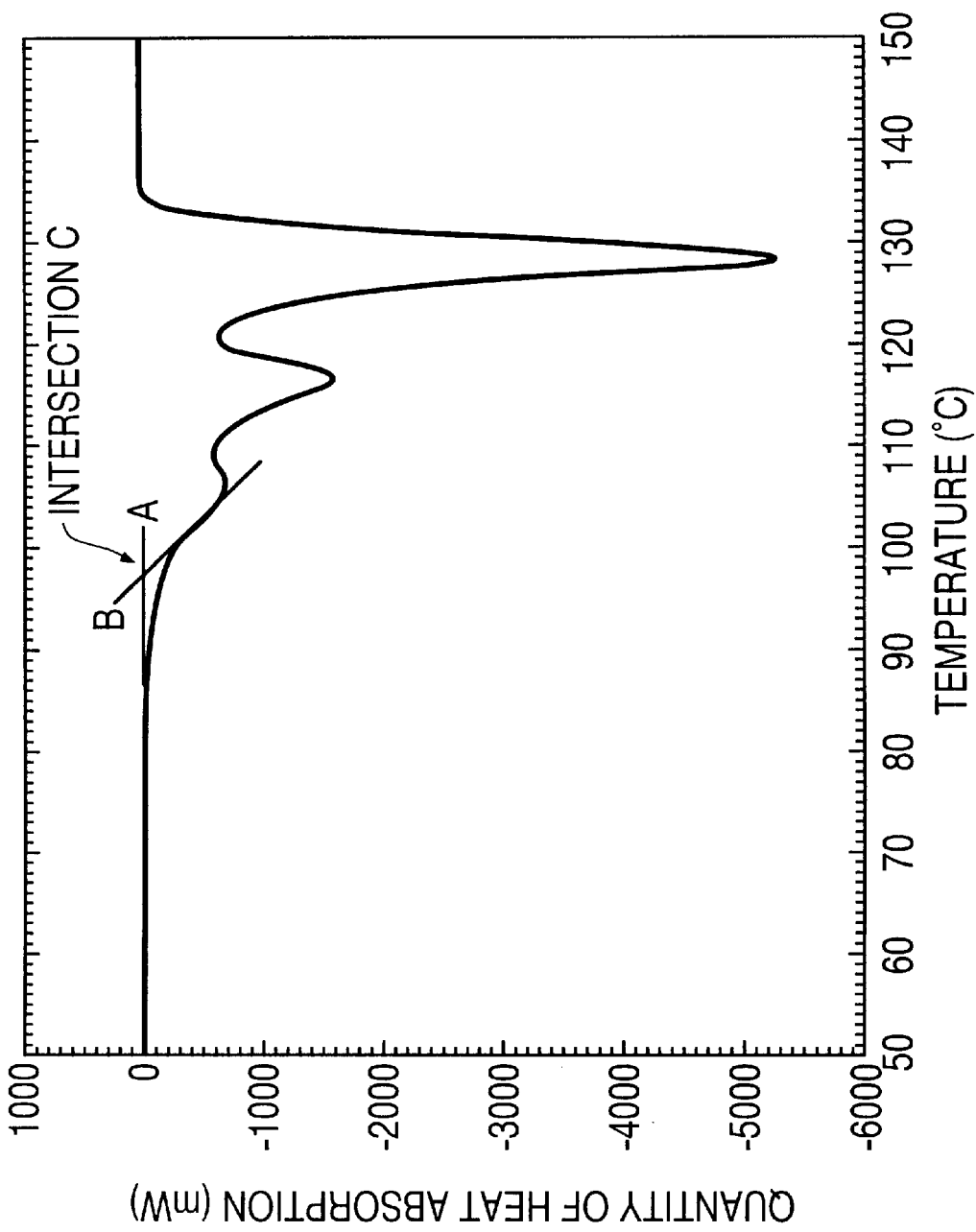
Figure 5:
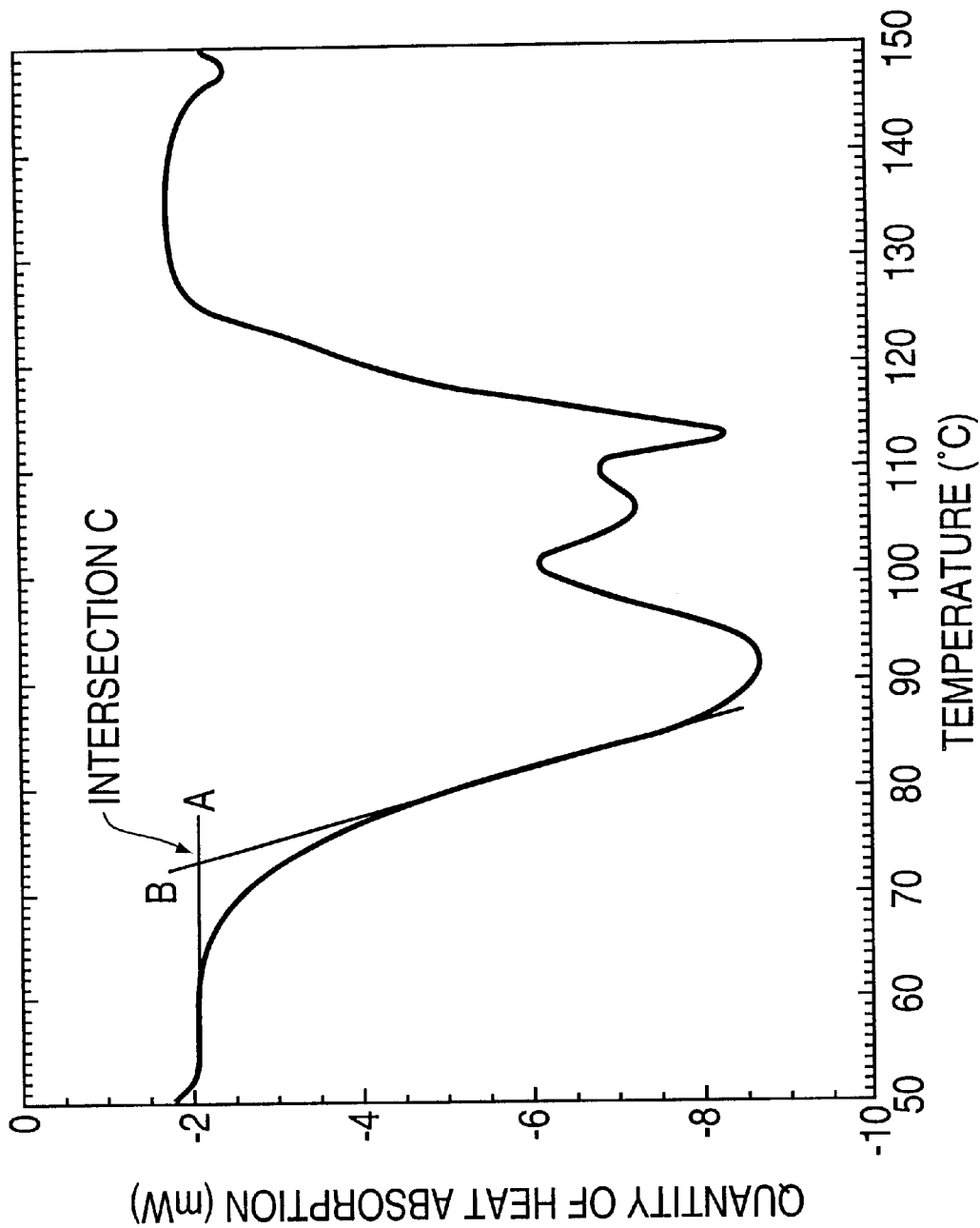

It is necessary in the present invention to mix the components (a) and (b) at a temperature lower, preferably by at least 5° C., than the starting temperature for crystal transition. By ths term "starting temperature for crystal transition" as used herein is meant the temperature at which the crystal structure begins to change. For instance, in FIG. 3 showing a heat absorption graph for zinc stearate through differential thermal analysis, the starting temperature for crystal transition of the zinc stearate is defined as the point of intersection C of the extension of the slope of the curve immediately before the start of heat absorption A and the extension of the slope of the curve immediately after the start of heat absorption B. As can be seen from FIG. 3, the starting temperature for crystal transition of zinc stearate is 100+ C. Likewise, the starting temperatures for crystal transition of calcium stearate in FIG. 4 and of magnesium stearate in FIG. 5 are 94° C. and 73° C., respectively. The starting temperature for crystal transition at the time of practical mixing, which varies depending upon the types of fatty acid chain and metal in the metallic soap to be obtained, is preferably 70 to 94° C. in the production of calcium stearate. The reaction, when carried out at a temperature lower than 70° C., enables the production of the objective material, but lowers the solubility of the starting material in the component (a), thus decreases the amount of the objective metallic soap based on the reaction solution, thereby deteriorating the production efficiency. On the other hand, the reaction, when carried out at a temperature higher than 94° C., will cause the flocculation of the metallic soap fine particles, thus enlarging the average particle size thereof.

The metallic soap slurry produced in the foregoing manner according to the present invention is separated into metallic soap cake and filtrate by the use of a conventional filtration apparatus. The resultant metallic soap cake is sufficiently washed with warm water or the like to decrease the amounts of impurities, and thereafter is treated by drying to form the objective metallic soap fine particles.

The drying treatment of the metallic soap cake is carried out at a temperature lower, preferably by at least 5° C., than the starting temperature for crystal transition of the objective metallic soap. The specific drying temperature, which varies depending upon the type of the objective metallic soap, is for instance, 100° C. or lower in the case of zinc stearate. The drying treatment thereof, when carried out at a temperature higher than the starting temperature for crystal transition thereof, will cause the flocculation of the metallic soap fine particles, thus enlarging the average particle size thereof.

The drying treatment of the metallic soap may be put into practice under atmospheric pressure or under reduced pressure or vacuum for efficient drying, or after a cleaning treatment of the metallic soap cake by means of a low boiling point solvent. The solvent to be used therein is preferably capable of efficiently removing water therefrom, and is exemplified by methanol, ethanol, acetone and methylene chloride.

In the above-mentioned manner, it is possible to easily produce the metallic soap fine particles which has an average particle size of at most 4 $\mu$m, which has a content of the particles having particle sizes larger than 10 $\mu$m of at most 4% by weight based on the entire particles, and which has the values ($R_C$–$R_A$) and/or ($R_D$–$R_B$) of at most 3 $\mu$m and/or at most 6 $\mu$m, respectivly. The metallic soap fine particles produced according to the present invention are in the form of plate, flake, bar, needle, lump, sphere, laminar or arborescent secondary-agglomerate or amorphous secondary-agglomerate. The average particle size or particle size of the metallic soap fine particles as mentioned herein are measured after the drying treatment without or prior to pulverization or classification.

In the following, detailed description will be given of the case where the metallic soap fine particles are used in a toner (developer) for an electrophotographic copying machine.

The process for producing the toner composition of the present invention by adding the metallic soap fine particles of the present invention to a toner, is not specifically limited, but there is preferably applied a conventional process for producing a toner in which a usual additive is added to the toner, for example, a process in which metallic soap is added before or during or after the preparation of toner particles.

In the case of adding to a toner, the metallic soap of the present invention, the amount of the metallic soap to be added is not specifically limited, but may be selected for use in the range of usually added amount. Specifically, the amount of the metallic soap is 0.05 to 50% by weight, preferably 0.1 to 50% by weight, more preferably 0.5 to 30% by weight, most preferably 2 to 30% by weight based on the amount of a toner resin. When two or more kinds of the metallic soap are used in combination, the total amount thereof shall be within the above-mentined range.

The developing method of the toner composition may be any of dry and wet systems. The dry developing method may be a well-known optional method such as a method using so-called binary developer, a method using unary magnetic developer and a method using unary non-magnetic developer.

A resin for toner is not specifically limited, but there is used a resin usually having a softening point of 150 to 200° C., that is, a simple resin such as styrenic resin, polyolefinic resin, acrylic resin and polyester resin, and a mixture of these resins.

There are usable additives that are usually added to the resin for toner and are other than the metallic soap. Examples thereof include a petroleum base long-chain hydrocarbon typified by paraffine wax and microcrystalline wax; a higher alcohol typified by dodecyl alcohol, lauryl alcohol, myristyl alcohol, palmityl alcohol, stearyl alcohol, arachyl alcohol and behenyl alcohol; a fatty acid typified by dodecanoic acid, lauric acid, myristic acid, palmitic acid, stearic acid, oleic acid, linoleic acid, ricinoleic acid, arachic acid, behenic acid, lignoceric acid, montanoic acid and selacholeic acid; a zinc salt, magnesium salt, calcium salt, cadmium salt or barium salt each of a dibasic acid such as succinic acid, maleic acid and fumaric acid; a higher fatty acid amide typified by palmitic acid amide, oleic acid amide, lauric acid amide, stearic acid amide, behenic acid amide, methylenebisstearamide, and ethylenebisstearamide; wax of natural origin comprising esters of long-chain fatty acids and alcohols, said wax being typified by carnauba wax, bees wax, montan wax, rice wax and candelilla wax; wax such as liquid or solid polyethylene wax, polypropylene wax, silicone wax, solid silicone wax and amide wax; polyhydric alcohol ester such as glycerol stearate, glycerol ricinolate, glycerol behenate, sorbitan stearate, propylene glycol stearate, pentaerythritol stearate and dipentaerythritol stearate; a fatty acid ester typified by maleic acid ethyl ester, maleic acid butyl ester, stearic acid ethyl ester, stearic acid butyl ester, palmitic acid cetyl ester, montanoic acid ethylene glycol ester, myristic acid myristyl ester, stearic acid stearyl ester and behenolic acid behenyl ester; partially saponified fatty acid ester such as montanoic acid ester partially saponified by calcium; an aliphatic fluorocarbon; a fluorine-containing surfactant; tetrafluoroethylene resin; an abrasive such as cerium oxide and silicon carbide; collidal silica; a fluidity-imparting agent such as aluminum oxide; a caking inhibitor; and a conductivity-imparting agent such as carbon black and tin oxide.

The toner which is used when the metallic soap is added thereto according to the present invention, may be any of a monochromic toner or color toner, and may be incorporated with a colorant according to the purpose of use of the toner composition. As the colorant usable in a toner, there are applicable all the pigments and dyes that have heretofore been used as a colorant for a toner.

Examples of black pigments include carbon black, cupric oxide, manganese dioxide, aniline black, activated carbon, non-magnetic ferrite and magnetite. Examples of yellow pigments include chrome yellow, zinc yellow, yellow iron oxide, cadmium yellow, mineral fast yellow, nickel-titanium yellow, navels yellow, naphthol yellow-S, Hansa yellow-G, Hansa yellow-10G, benzidine yellow-G, benzidine yellow-GR, quinoline yellow-lake, permanent yellow-NCG and Tartrazine lake. Examples of orange-color pigments include red chrome yellow, molybdenum orange, permanent orange-GTR, pyrazolone orange, vulcan orange, benzidine orange G, indanthrene brilliant orange RK and indanthrene brilliant orange GK. Examples of red pigments include red iron oxide, cadmium red-red lead, mercury sulfide, cadmium, permanent red 4R, lithol red, pyrazolone red, watchung red, calcium salt, lake red C, lake red D, brilliant carmine 6B, brilliant carmine 3B, eosine lake, Rhodamine lake B and alizarin lake. Examples of blue pigments include iron blue, cobalt blue, alkali blue lake, Victoria blue lake, phthalocyanine blue, non-metallic phthalocyanine blue, phthalocyanine blue-chlorine compound in part, fast sky blue and indanthrene blue BC. Examples of violet pigments include manganese violet, fast violet B and methyl violet lake. Examples of green pigments include chromium oxide, chromium green, pigment green-B, malachite green lake and final yellow-green G. Examples of white pigments include zinc oxide, titanium oxide, antimony white and zinc sulfide. Examples of extender pigments include barytes powder, barium carbonate, clay, silica, white carbon, talc and white alumina.

Examples of dyes include various dyes such as basic dye acidic dye, disperse dye and direct dye, e.g. nigrosine, methylene blue, rose bengal, quinoline yellow and ultramarine blue.

Any of these colorants may be used alone or in the form of a mixture or a solid solution, and is selected taking into consideration the hue angle, chroma, lightness, weatherability, transparency on OHP film and dispersibily in toner particles. The amount of the colorant to be added is selected in the range of usually 1 to 20 parts by weight based on 100 parts by weight of the toner resin. However, different from other colorants, a magnetic material, when used as a black colorant, is added in the range of usually 30 to 150 parts by weight based on 100 parts by weight of the toner resin. Moreover, in the case where use is made of the toner composition for an electrophotographic copying machine of the present invention as a light-transmittable color toner, a variety of pigments and dyes as mentioned hereunder are usable as a colorant.

Examples of yellow pigments include C.I. 10316 (naphthol yellow-S), C.I. 11710 (Hansa yellow-10G), C.I. 11660 (Hansa yellow-5G), C.I. 11670 (Hansa yellow-3G), C.I. 11680 (Hansa yellow-G), C.I. 11730 (Hansa yellow-GR), C.I. 11735 (Hansa yellow-A), C.I. 117408 (Hansa yellow-RN), C.I. 12710 (Hansa yellow-R), C.I. 12720 (pigment yellow-L), C.I. 21090 (benzidine yellow), C.I. 21095 (benzidine yellow-G), C.I. 21100 (benzidine yellow-GR), C.I. 22040 (permanent yellow-NCG), C.I. 21220 (vulcan fast yellow-5) and C.I. 21135 (vulcan fast yellow-R).

Examples of red pigments include C.I. 12055 (Sterlin I), C.I. 12075 (permanent orange), C.I. 12175 (lithol fast orange), C.I. 12305 (permanent orange-GTR), C.I. 11725 (Hansa yellow-3R), C.I. 21165 (vulcan fast orange-GG), C.I. 21110 (benzidine orange-G), C.I. 12120 (permanent red-4R), C.I. 1270 (pera red), C.I. 12085 (fire red), C.I. 12315 (brilliant fast scarlet), C.I. 12310 (permanent red-F2R), C.I. 12335 (permanent red-F4R), C.I. 12440 (permanent red-FRL), C.I. 12460 (permanent red-FRLL), C.I. 12420 (permanent red-F4RH), C.I. 12450 (light fast red toner-B), C.I. 12490 (permanent carmine-FB) and C.I. 15850 (brilliant carmine-6B). Examples of blue pigments include C.I. 74100 (non-metallic phthalocyanine blue), C.I. 74160 (phthalocyanine blue) and C.I. 74180 (fast sky blue).

Moreover, a binary developer, when used in the toner composition of the present invention, may be mixed with carrier powders. In this case, all well-known carriers are usable. Examples of the carriers include magnetic powders such as iron powders, ferrite powders and nickel powders, glass beads and the aforesaid powders the surfaces of which are treated with a resin or the like.

A magnetic toner containing a magnetic material is usable in the toner composition of the present invention. Examples of the magnetic material to be contained in the magnetic toner include an iron oxide such as magnetite, hematite and ferrite; a metal such as cobalt, nickel and iron; an alloy of any of said metals and a metal such as aluminum, copper, lead, magnesium, tin, zinc, antimony, berylium, bismuth, cadmium, calcium, manganese, selenium, titanium, tungsten and vanadium, and mixtures thereof.

In the following, detailed description will be given of the case where metallic soap according to the present invention is used as a cleaning aid for a picture-image recording apparatus such as an electronic copying machine.

The cleaning aid according to the present invention, which comprises at least said metallic soap, may comprise only said metallic soap or may comprise a conventional cleaning aid in combination. For instance, said metallic soap is usable in combination with a conventional cleaning aid such as teflon, methyl methacrylate, polytetrafluoroethylene resin, polyfluorovinylidene resin, molybdenum sulfide, graphite, boron nitride, selenium oxide, ferric oxide or alumina oxide. The amount of said metallic soap to be used in combination with a conventional cleaning aid is not specifically limited, but is preferbaly an amount which is customarily selected in adding said metallic soap. Specifically the amount thereof is preferably in the range of 1 to 80% by weight based on the entire amount of the cleaning aid composition.

Figure 6:
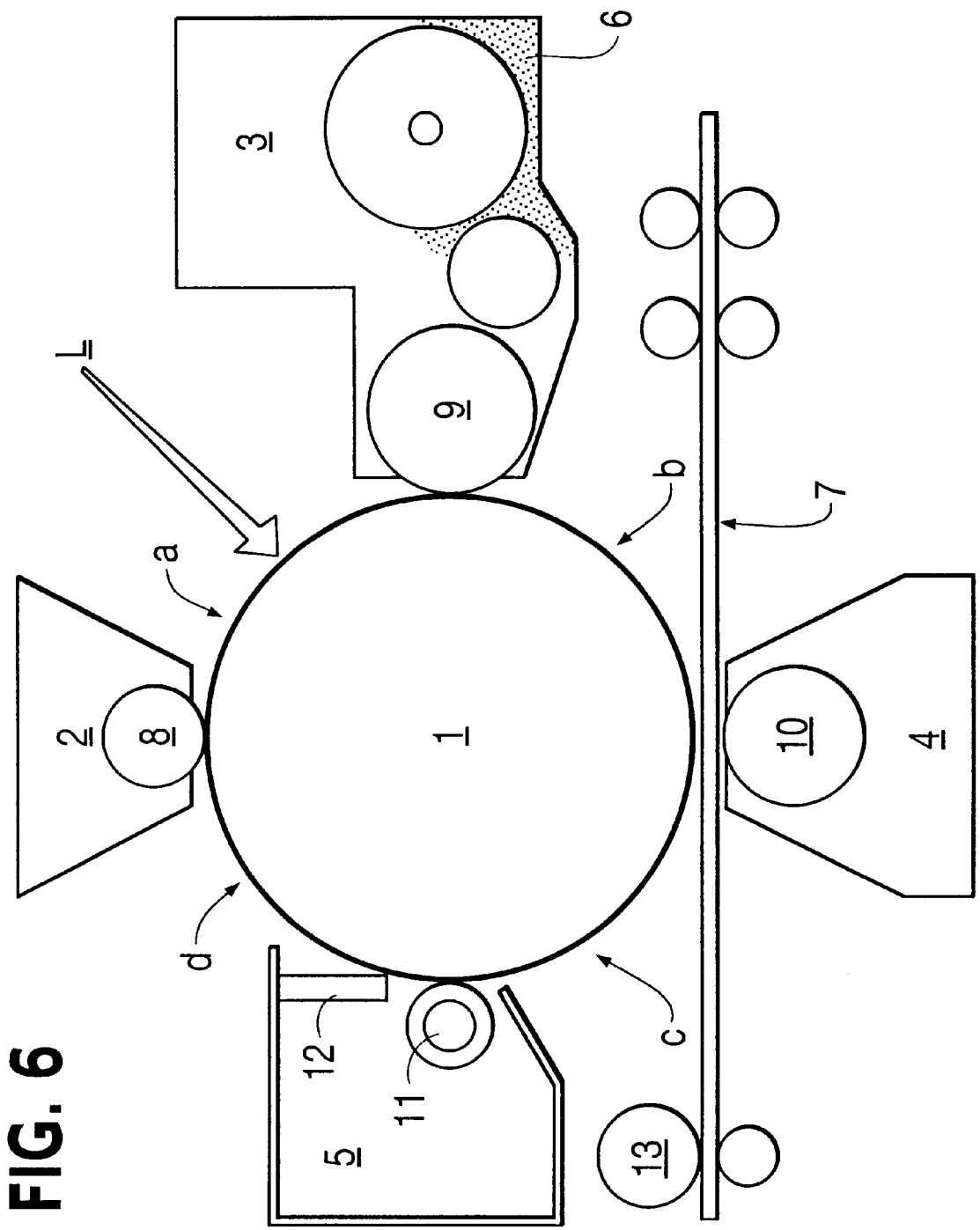

In the case where the cleaning aid according to the present invention is applied onto the surface of a picture image support, the place at which an apparatus for coating the surface of a picture-image support (coating apparatus) is installed is not specifically limited. For example, in FIG. 6 showing a schematic view of a picture-image forming apparatus, the coating apparatus may be installed between an electrification apparatus 2 and a developing apparatus 3(a), between the developing apparatus 3 and a tranfer apparatus 4(b), between the transfer apparatus 4 and a cleaning apparatus 5(c) and between the cleaning apparatus 5 and the electrification apparatus 2(d). Further, an electrification apparatus 2, a developing apparatus 3, a transfer apparatus 4 or a cleaning apparatus 5 may be imparted with a function of coating the surface of a picture image support 1 with the cleaning aid. There are available, for example, a method in which the surface of an electrification roller 8 in the electrification apparatus 2 is coated with the cleaning aid in the form of a solid to cause the electrification roller 8 to frictionally slide on the picture image support 1; a method in which the surface of a developing roller 9 in the developing apparatus 3 is coated with the cleaning aid in the form of a solid to cause the developing roller 9 to frictionally slide on the picture image support 1; a method in which a cleaning brush 11 or a blade 12 in the cleaning apparatus 5 is coated with the cleaning aid in the form of powder or dispersion to cause the cleaning brush 11 or the blade 12 to frictionally slide on the picture image support 1; and a method in which a cleaning aid is placed on the portion at which the blade 12 frictionally slides on the picture image support 1 to cause the blade 12 to frictionally slide on the picture image support 1. Of these is particularly preferable a method in which the apparatus for coating the cleaning aid of the present invention is installed between the cleaning apparatus 5 and the developing apparatus 3. In the case of using an electrification method by causing an electrification brush to frictionally slide on the surface of the picture image support, it is preferable to install a coating apparatus for the cleaning aid between the downstream side of the electrification brush and the developing apparatus 3. Apparatuses for coating the surface of the picture image support with the cleaning aid may be installed at a plurality of places.

The developer and developing apparatus usable in the present invention are not specifically limited. The developing apparatus may be a monochromic or color image-forming aparatus of dry or wet system by using a known developer such as a binary, unary magnetic or unary non-magnetic developer. There are usable in combination therewith, the picture-image forming apparatuses and developers as described, for instance, in the schematic drawings and working examples of Japanese Patent Application Laid-Open Nos. 165680/1985 (Sho-60), 225870/1985 (Sho-60), 160761/1986 (Sho-61), 13558/1989 (Sho-64), 269478/1991 (Hei-3), 276764/1992 (Hei-4), 119676/1993 (Hei-5), 35155/1993 (Hei-5), 160165/1995 (Hei-7), 56390/1995 (Hei-7), 180860/1995 (Hei-7), 271262/1995 (Hei-7), 137354/1996 (Hei-8), 297376/1996 (Hei-8) and the like.

In the case of the surface of the picture image support being coated with the cleaning aid according to the present invention, the form of the cleaning aid is not specifically limited, but is exemplified by solid, wax, block formed by compacting powders, powder and dispersion using a solvent. In the case of the cleaning aid of the present invention being in the form of solid or block, it is molded into the form of flake, plate or roll. The resultant molding is arranged so that it is supported with a supporting member fixed on the body of a copying machine and the tip of the cleaning aid frictionally slides on the picture image support. In the case of the cleaning aid of the present invention being in the form of powder or dispersion using a solvent, it is uniformly applied on the surface of the picture image support with a coating apparatus which is supported with a supporting member fixed on the body of a copying machine. The coating apparatus is not specifically limited, but is exemplified by a sponge roll, pad, roll-type brush, brush and rubber roll.

The cleaning method to be used in the present invention is not specifically limited, but there is available a method by allowing a blade, cleaning brush, magnetic brush or web to frictionally slide on the picture image support so as to clean up the residual toner. The direction of frictional sliding on the picture image support may be cocurrent, countercurrent or crosscurrent to the movement direction of the picture image support.

The method for forming a toner image on a picture image support is not specifically limited, but is exemplified by a cascade developing method, a developing method with a magnetic brush, a non-contact developing method under applied alternate voltage and a spray developing method.

As a method in which a visible image prepared on picture image support is transferred from said support to a recording medium, and thereafter a toner is fixed onto the recording medium, there are available conventional known heat-fixing methods, which are specifically exemplified by a non-contact heat-fixing method such as an open system heat-fixing method and a flash heat-fixing method; a heat and pressure-fixing method by means of an elastic body or a rigid roller; and a combinational method thereof. In practice, the heating temperature is selected according to the fixing speed and paper quality. The use of the toner composition of the present invention, when compared with the use of conventional toners, well enables fixing at a lower energy, keeps favorable non-offset properties even in the use of a contact type fixing apparatus and besides, expands the selectivity of the materials of construction for a contact type fixing apparatus.

A photosensitizer to be used in the picture image support according to the present invention, can be selected for use from the conventional photosensitizers, which are exemplified by a binder type photosensitizer such as zinc oxide and cadmium sulfide, a selenium base photosensitizer, an amorphous silicon base photosensitizer, a photosensitizer using a photo-conductive semiconductor such as an organic photosensitizer and a PIP system photosensitizer equipped with an insulating layer on said photosensitizer.

The cleaning aid of the present invention is also applied to an electrostatic recording apparatus of the type in which a picture image support is composed of a dielectric, and is electrified in the form of a picture image by a letter electrode or a needle electrode, and also to a magnetic recording apparatus of the type in which a picture image support is composed of a magnetism-sensitive member in which magnetic powders are dispersed in a binding resin, said magnetism-sensitive member being imparted with magnetic signals to form magnetic latent image, and said magnetic latent image being developed with a magnetic developer.

The cleaning aid of the present invention can be used in combination with the toner 6 for an electronic copying machine. The method for incorporating the cleaning aid in the toner is not specifically limited, and it may be a conventional method for incorporating an additive. There is available, for example, a method in which the cleaning aid is added prior to, during or after the preparation of toner particles. The above-mentioned toner composition can be used in combination with a coating apparatus for other cleaning aid to be used in the present invention. The cleaning aid of the present invention, when added to a toner, is not specifically limited with regard to the amount of addition, but is preferably added thereto in a usual amount of a conventionally used cleaning aid, for instance, 2 to 50% by weight based on a toner resin.

The toner developing method may be any of dry system and wet system. The dry developing method may be an optional known method such as a method using a binary developer, a unary developer, a magnetic unary developer or a non-magnetic unary developer.

The metallic soap fine particles according to the present invention which are markedly fine and have a narrow particle size distribution, are extremely useful for improving the fluidity of metallic powders accompanying the complication of the shape of a casting; for finely graining developing toner particles accompanying the steady trend toward high resolution of electonic printers such as an electronic copying machine; for finely graining additives for coating materials accompanying the steady trend toward extremely thinned coating film; and for finely graining solid contents of cosmetics accompanying the enhancement in spreadability of cosmetics.

In addition, according to the process for producing the metallic soap fine particles of the present invention, it is made possible to produce metallic soap fine particles which are markedly fine and have a narrow particle size distribution in a simple, easy and efficient manner.

Moreover, the toner composition for an electronic copying machine which comprises said metallic soap fine particles is capable of improving blocking resistance of the toner, fluidity thereof and eliminability thereof from a picture image support without impairing the surface of the picture image support in an electrophotographic copying machine; forming satisfactory visible image on the picture image support; and enhancing the cleaning performance for the toner stuck to the picture image support.

Further, the cleaning aid which comprises said metallic soap fine particles and is used for an electronic copying machine such as an picture-image recording apparatus, is capable of improving eliminability of the toner from a picture image support without impairing the surface of the picture image support in an electrophotographic copying machine; and enhancing the cleaning performance for the residual toner stuck to the picture image support by adopting a method in which the picture image support is coated directly with said metallic soap fine particles having a specific particle size, or the like method.

In the following, the present invention will be described in more detail with reference to comparative examples and non-limitative working examples.

EXAMPLES 1 TO 11 & COMPARATIVE EXAMPLES 1 TO 3

By the use of the starting materials 1 and 2 as shown in Table 1, the components (a) and (b) were prepared. The concentrations of the starting materials 1 and 2 are given in Table 2. The components (a) and (b) were mixed with each other by the following mixing method A or B so as to make a total amount of 500 g of metallic soap. The temperature at the time of mixing, mixing method and equivalent ratio (a/b) of fatty acid salts in the component (a) to inorganic acid salts in the component (b) are given in Table 2.

(Mixing method A)

There was provided a 2 l receiving vessel equipped with a stirrer having a turbine blade with a diameter of 6 cm, and the turbine blade was rotated at 350 r.p.m. The receiving vessel was charged at the same time with the components (a) and (b) regulated to temperatures as shown in Table 2 in different directions so as to finish total charge thereof within 10 minutes. After the completion of the total charge, maturing was carried out for 10 minues at the same reaction temperature to complete the reaction and produce a metallic soap slurry.

Subsequently, the resultant metallic soap slurry was filtered into a metallic soap cake, which was washed with water twice and followed by washing with a solvent as shown in Table 2. The metallic soap cake thus obtained was dried under the drying conditions as shown in Table 2 to produce metallic soap fine particles. The starting temperature for crystal transition of the resultant metallic soap fine particles is given in Table 2.

(Mixing method B)

There were provided a pipe-line homogenizer capable of feeding and mixing the components (a) and (b) separately by means of a fixed delivery pump, and a 2 l receiving vessel equipped with a stirrer having a turbine blade with a diameter of 6 cm. The turbine blade was rotated at 350 r.p.m. The pipe-line homogenizer was charged separately with the components (a) and (b) regulated to temperatures as shown in Table 2, and the resultant mixture discharged from the pipe-line homogenizer was fed in the receiving vessel, while the flow rates of the solutions of the components were adjusted with the fixed delivery pump so as to simultaneously finish the feed of total amount of each of the solutions within 10 minutes. After the completion of the total feed, maturing was carried out for 10 minues at the same reaction temperature to complete the reaction and produce a metallic soap slurry.

Subsequently, the resultant metallic soap slurry was filtered into a metallic soap cake, which was washed with water twice and followed by washing with a solvent as shown in Table 2. The metallic soap cake thus obtained was dried under the drying conditions as shown in Table 2 to produce metallic soap fine particles. The starting temperature for crystal transition of the resultant metallic soap fine particles is given in Table 2.

COMPARATIVE EXAMPLES 4 TO 5

By the us e of the starting materials 1 and 2 as shown in Table 1, the components (a) and (b) were prepared. The concentrations of the starting materials 1 and 2 are given in Table 2. The components (a) and (b) were used to produce metallic soap fine particles by the double decomposition process or fusion process as described hereunder. The temperature at the time of mixing, mixing method and equivalent ratio (a/b) of fatty acid salts in the component (a) to inorganic acid salts in the component (b) are given in Table 2.

COMPARATIVE EXAMPLE 4

Double Decomposition Process

There was provided a 2 l receiving vessel equipped with a stirrer having a turbine blade with a diameter of 6 cm, and the turbine blade was rotated at 350 r.p.m. The receiving vessel was charged with the component (a), which was regulated to the temperature as shown in Table 2. Subsequently, the component (b) as shown in Table 2 was added dropwise to the receiving vessel over a period of 30 minutes. After the completion of the total charge, maturing was performed for 10 minues at the same reaction temperature to complete the reaction and produce a metallic soap slurry.

Subsequently, the resultant metallic soap slurry was filtered into a metallic soap cake, which was washed with water twice and followed by washing with a solvent as shown in Table 2. The metallic soap cake thus obtained was dried under the drying conditions as shown in Table 2 to produce metallic soap fine particles. The starting temperature for crystal transition of the resultant metallic soap fine particles is given in Table 2.

COMPARATIVE EXAMPLE 5

Fusion Process

There was provided one l enclosable vessel-type reactor equipped with a stirrer capable of kneading a high viscosity substance. Then 500 g of the component (a) as shown in Table 2 was placed in the reactor. Thereafter the stirrer was rotated at 50 r.p.m., and the content therein was regulated to the temperature as shown in Table 2. Then to the reactor were placed 68 g of the component (b) as shown in Table 2 and water in an amount of 2% by weight based on the component (a), and the reactor was enclosed. The reaction was carried out for 180 minutes, while the stirrer was rotated to complete the reaction.

Subsequently, the metallic soap powders obtained in the above manner were sufficiently pulverized with a mixer. The resultant metallic soap powders were classified into metallic soap fine particles by the use of a JIS standard sieve having a degree of opening of 45 $\mu$m.

Measurement of Particle Shape using Electron Microscope

Figure 7:
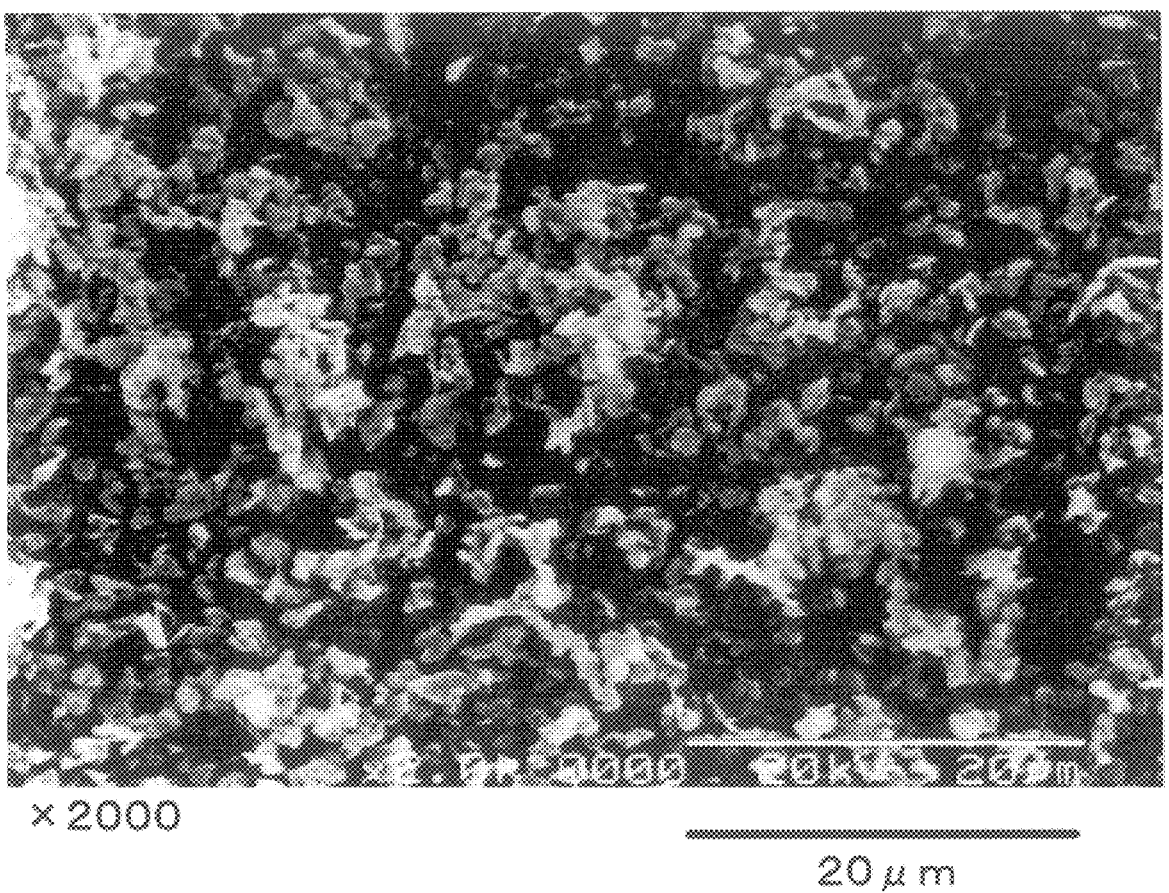
Figure 8:
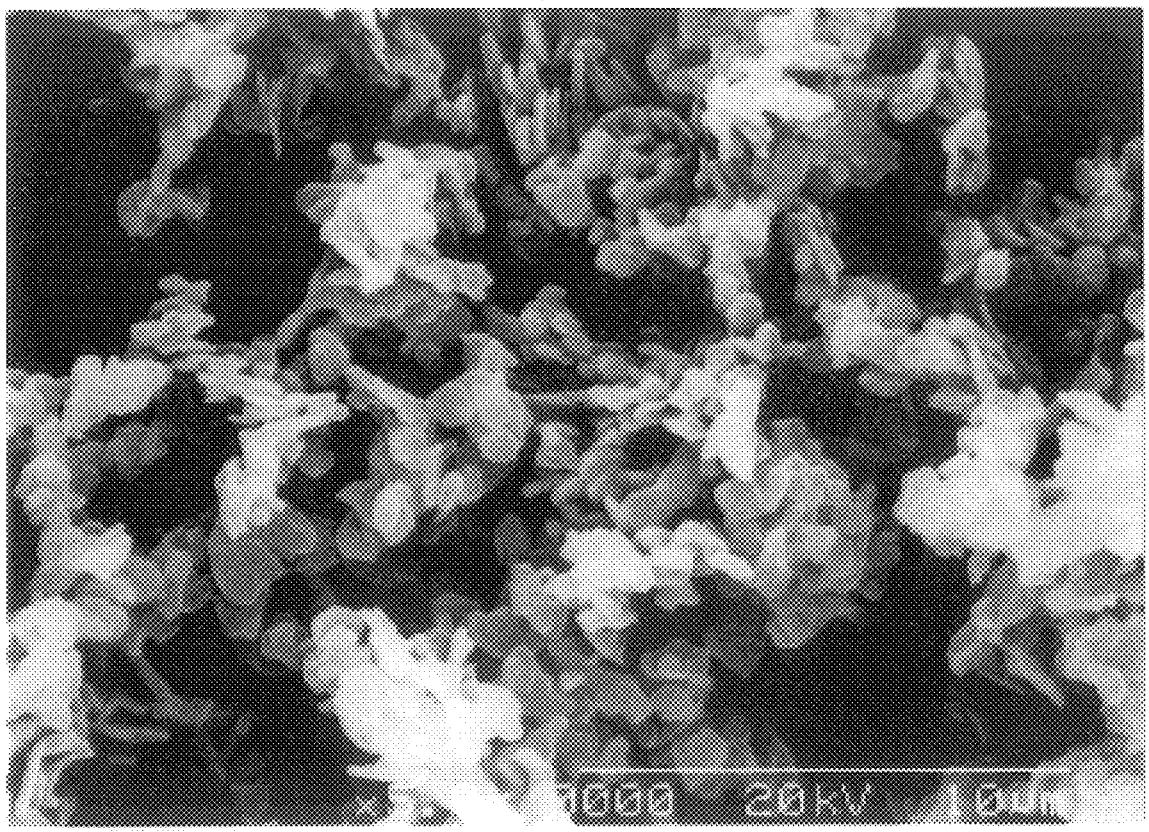
Figure 9:
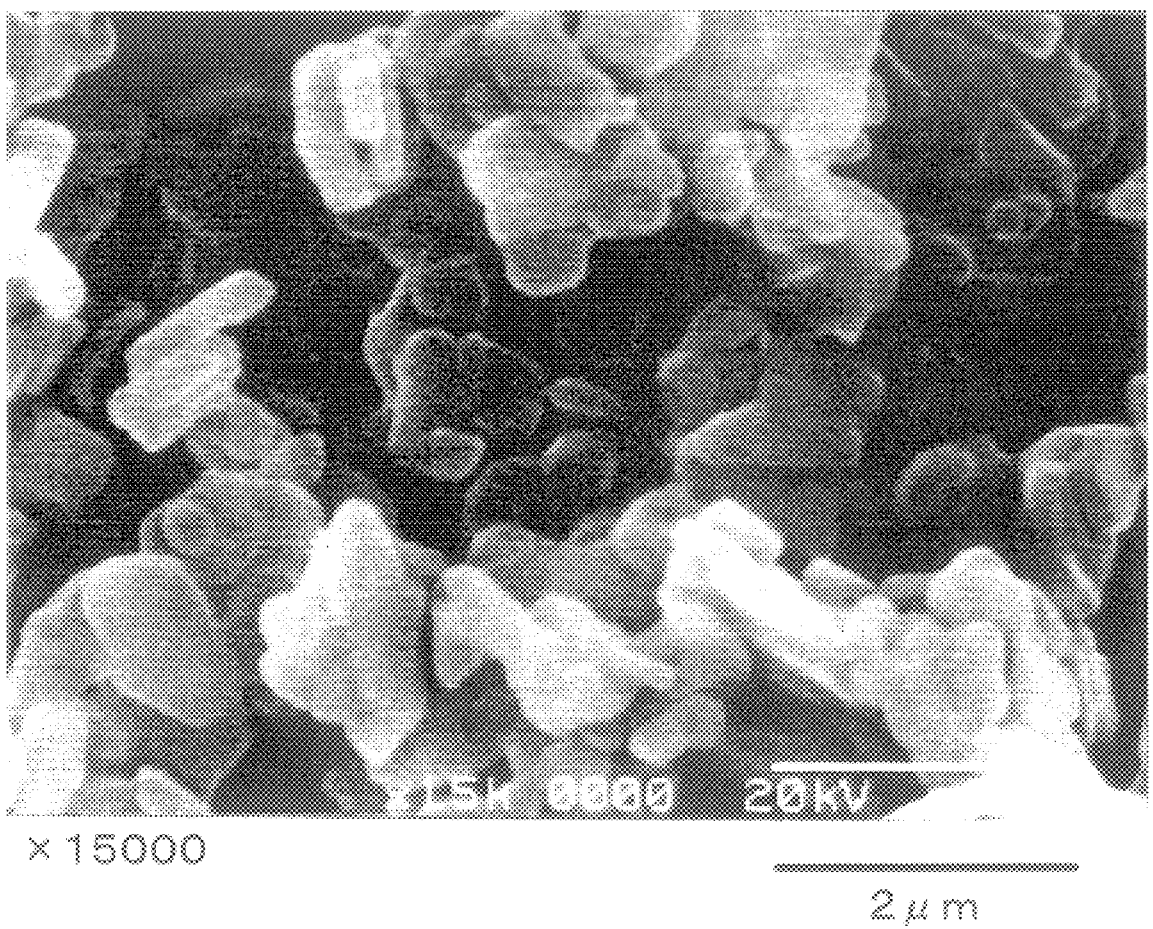
Figure 10:
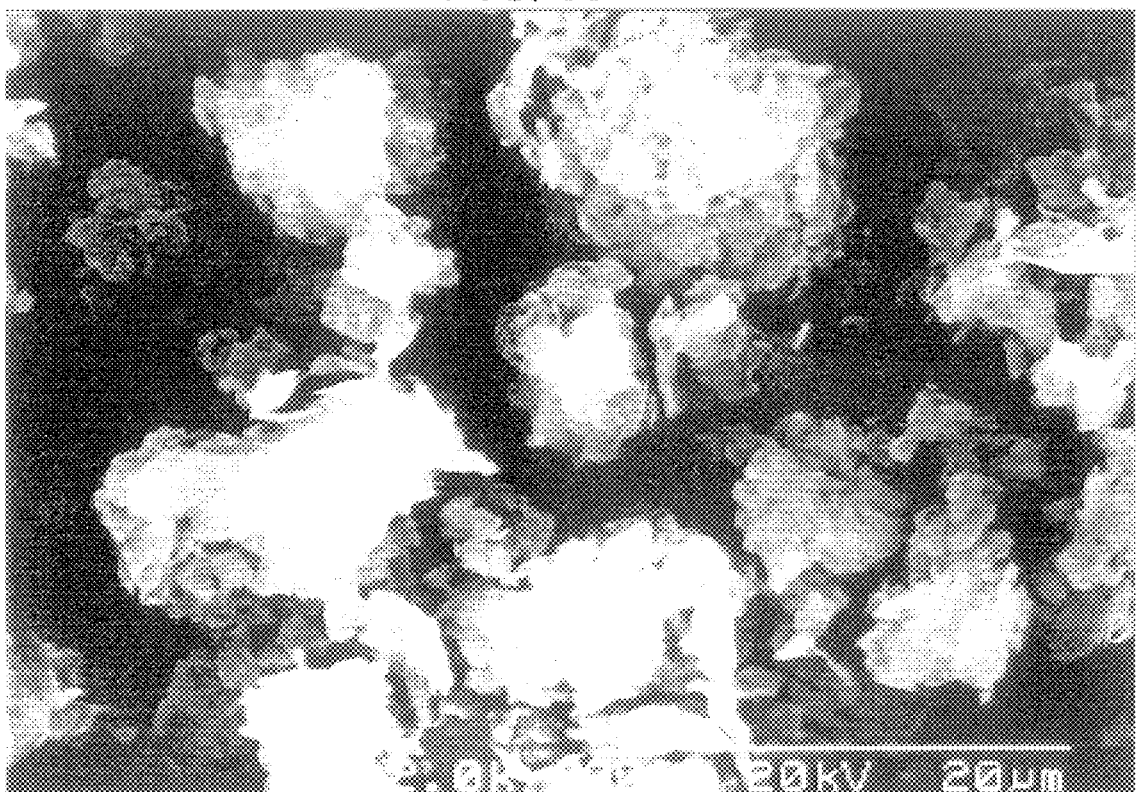

The metallic soap fine particles thus obtained were photographed through a Scanning Electron Microscope (SEM) S-2100A produced by Hitachi, Ltd. in order to visually confirm the particle conditions thereof. FIGS. 7, 8 and 9 illustrate the electrophotographs at magnifications of 2000, 5000 and 15000, respectively of the metallic soap fine particles prepared in Example 3. FIG. 10, illustrates the electrophotograph at a magnification of 2000 of the metallic soap fine particles prepared in Comparative Example 4.

Measurement of Particle Size Distribution

Ethanol in an amount of 10 mg was added to 0.5 g of the metallic soap fine particles obtained in the above-mentioned manner, and ultrasonic dispersion was carried out for 5 minutes by the use of a ultrasonic dispersion instrument produced by Nihonseiki Kaisha Ltd. Subsequently, the resultant metallic soap fine particles in the form of dispersion were added to a micro-track particle size distribution-measuring apparatus (Model SPA) produced by NIKKISO Ltd. in which ethanol was circulated as a measuring solvent until the DV value reached 0.6 to 0.8 to measure the particle size distribution of each of the samples under said condition.

In Table 3 are given the contents of the metallic soap in each of the slurries thereof prepared in the present examples and comparative examples (% by weight), yield (g) and yield rate (% by weight) of the same; are also given average particle sizes ($\mu$m), $R_A$ ($\mu$m), $R_B$ ($\mu$m), $R_C$ ($\mu$m), $R^D$ ($\mu$m), $R_C$–$R_A$ ($\mu$m), $R_D$–$R_B$ ($\mu$m), and contents of particles having sizes larger than 10 $\mu$m (% by weight) based on the entire amount of the metallic soap fine particles regarding each of the collected samples; and are given the cumulation amounts (% by weight) of particles for each of the collected samples at 0.34 $\mu$m, 0.66 $\mu$m, 1.01 $\mu$m, 3.73 $\mu$m, 5.27 $\mu$m, 10.55 $\mu$m, 21.10 $\mu$m and 42.21 $\mu$m. It can clearly be confirmed from the results of the particle size distribution measurements that the results in Examples 1 to 10 demonstrate high yields, small average particle size and narrow particle size distribution in comparison with those in Comparative Examples 1 to 5. Likewise, it is evidently understood from the results of electrophotographs through an electron microscope that the metallic soap according to the present invention (FIGS. 7, 8 and 9) is substantially free from large-sized particles, has extremely fine particles, and is uniform in particle size distribution as compared with Comparative Examples 1 to 5.

In the following, some description will be given of non-limitative working examples according to the present invention in which the above-mentioned metallic soap fine particles are used in a toner for an electronic copying machine and further of preparation examples of toner compositions to be used in working examples according to the present invention and in comparative examples.

PREPARATIN EXAMPLE 1

Polyester resin having a softening point of 85° C. in an amount of 95 parts by weight, 5 parts by weight of carnauba wax, 8 parts by weight of carbon black and 3 parts by weight of glocine dye were fusedly kneaded, cooled, then coarsely crushed with a hammer mill, and subsequently pulverized with a pulverizer of air jet system. The resultant pulverized product was classified into particles having an average particle size of 9 $\mu$m. To 100 parts by weight of the resultant particles was added under mixing, one part by weight of titanium oxide fine particles having an average particle size of 0.02 $\mu$m to produce unary magnetic toner particles.

PREPARATIN EXAMPLE 2

In an autoclave equipped with a thermometer and a stirrer were fed 94 parts by weight of dimethyl terephthalate, 95 parts by weight of dimethyl isoterephthalate, 89 parts by weight of ethylene glycol, 80 parts by weight of neopentyl glycol and 0.1 parts by weight of zinc acetate. The resultant mixture was heated to 120 to 230° C. for 120 minutes to carry out transesterification. Subsequently, 8.4 parts by weight of 5-sodium sulfoisophthalate was added to the reactants, while the reaction was continued at 220 to 230° C. for 60 minutes. After the reaction temperature was raised to 250° C., the reaction was further continued at a reaction pressure of 1 to 10 mmHg for 60 minutes. As a result, there was obtained emulsified dispersion of copolyester.

To 1 l of the above-obtained dispersion was added 30 ml of jojoba wax emulsion (solid content of 30% by weight) to prepare a mixture, which was added dropwise to 2 l of 0.2% aqueous solution of $MgSO_4$ under heating to 40° C. and sufficient stirring over a period of about 30 minutes to proceed with granulation operation. The resultant granulated product was thermally insulated for 30 minutes, and then cooled to ordinary temperature. A stainless steel-made pot was charged with 100 g of aqueous dispersion of the resultant polyester resin particles incorporated with a release agent, and 3 g of C.I. disperse yellow 64. The resultant mixture was heated to raise the temperature up to 130° C. at a temperature raising rate of 3° C./minute, maintained thereat for 60 minutes, and thereafter cooled to ordinary temperature. The dyed particles thus obtained were filtered, cleaned and dried with a spray dryer to produce yellow-colored resin particles. Subsequently by using C.I. disperse red 92 as magenta and C.I. disperse blue 60 as cyanide in the same manner as above, there were obtained resin particles dyed with magenta and cyanide, respectively. To 100 g of the dyed resin particles was added 1 g of silica to produce a yellow toner, a magenta toner and cyanide toner. Then, 100 g of silicon-coated ferrite beads were mixed with 5 g of each of the yellow toner, magenta toner and cyanide toner to produce a binary toner.

EXAMPLES 12 TO 16 & COMPARATIVE EXAMPLES 6 TO 13

The metallic soap fine particles according to the present invention were added to each of the toners prepared in Preparation Examples 1 to 2, and the resultant mixture was uniformly mixed with a mixer. Then each of the toner compositions thus prepared was filled in a copying machine to proceed with picture image formation. Thus evaluations were made of the conditions of the printed matters prepared at the time of picture image formation. Further, evaluations were made of the printing stability at the time of running test in the copying machine, the conditions of the printed matters at the end of the running test, the conditions of slidable friction for the surface of the picture image support in the copying machine and the conditions of cleaning for the picture image support. Furthermore, evaluations were made of the blocking resistance at the time of preservation at elevated temperatures for each of the toner compositions that had been evaluated in the aforesaid items.

EXAMPLE 12

To 100.0 parts by weight of the toner prepared in Preparation Example 1 was added 1 part by weight of zinc stearate which was free from particles having a particle size larger than 10 μm, which had an average particle size of 1.3 μm and which had the values $(R_C-R_A)$ and $(R_D-R_B)$ of 1.51 μm and 2.21 μm, respectively. The aforesaid toner composition was placed on a monochromic copying machine available from the market (produced by CANON Inc. under the trade name "LBP404G") to proceed with picture image formation. As a result, there was obtained a vivid picture image with a high density free from surface contamination. Even after 20,000 sheets of picture image forming operation, a favorable cleaning condition was maintained without impairing the surface of the picture image support. Thereafter, the toner composition was left standing at 50° C. for 2 months, but no blocking of the toner composition was confirmed. Then picture image formation was performed by using the toner composition. As a result, as was the case with the picture image formation test before said standing, there was obtained a vivid picture image with a high density free from surface contamination.

EXAMPLE 13

To 100.0 parts by weight of the toner prepared in Preparation Example 1 was added 7 parts by weight of a mixture of calcium myristate and calcium stearate (1:1 by weight) which was free from particles having a particle size larger than 10 μm, which had an average particle size of 1.8 μm and which had the values $(R_C-R_A)$ and $(R_D-R_S)$ of 1.73 μm and 2.38 μm, respectively. The aforesaid toner composition was placed on a monochromic copying machine available from the market (produced by CANON Inc. under the trade name "LBP404G") to proceed with picture image formation. As a result, there was obtained a vivid picture image with a high density free from surface contamination. Even after 20,000 sheets of picture image forming operation, a favorable cleaning condition was maintained without impairing the surface of the picture image support. Thereafter, the toner composition was left standing at 55° C. for 1 month, but no blocking of the toner composition was confirmed. Then picture image formation was performed by using the toner composition. As a result, as was the case with the picture image formation test before said standing, there was obtained a vivid picture image with a high density free from surface contamination.

EXAMPLE 14

To 100.0 parts by weight of the toner prepared in Preparation Example 1 was added 0.5 part by weight of a mixture of barium stearate and zinc stearate (3:1 by weight) which was free from particles having a particle size larger than 10 μm, which had an average particle size of 2.0 μm and which had the values $(R_C-R_A)$ and $(R_D-R_D)$ of 1.50 μm and 2.18 μm, respectively. The aforesaid toner composition was placed on a monochromic copying machine available from the market (produced by CANON Inc. under the trade name "LBP404G") to proceed with picture image formation. As a result, there was obtained a vivid picture image with a high density free from surface contamination. Even after 20,000 sheets of picture image forming operation, a favorable cleaning condition was maintained without impairing the surface of the picture image support. Thereafter, the toner composition was left standing at 60° C. for 1 month, but no blocking of the toner composition was confirmed. Then picture image formation was performed by using the toner composition. As a result, as was the case with the picture image formation test before said standing, there was obtained a vivid picture image with a high density free from surface contamination.

EXAMPLE 15

To 100.0 parts by weight of each of the color toner prepared in Preparation Example 2 was added 1 part by weight of a mixture of magnesium stearate and calcium behenate (2:1 by weight) which was free from particles having a particle size larger than 10 μm, which had an average particle size of 0.8 μm and which had the values $(R_C–R_A)$ and $(R_D–R_B)$ of 0.45 μm and 2.51 μm, respectively. The aforesaid toner composition was placed on a color copying machine available from the market (produced by Hitachi Ltd. under the trade name "HITACHI HT-4551-11") to proceed with picture image formation. As a result, there was obtained a vivid picture image with a high density free from surface contamination. Even after 20,000 sheets of picture image forming operation, a favorable cleaning condition was maintained without impairing the surface of the picture image support. Then the toner composition was left standing at 50° C. for 1 month, but no blocking of the toner composition was confirmed. Then picture image formation was performed by using the toner composition. As a result, as was the case with the picture image formation test before said standing, there was obtained a vivid picture image with a high density free from surface contamination.

EXAMPLE 16

To 100.0 parts by weight of the toner prepared in Preparation Example 2 was added 10 parts by weight of zinc behenate which was free from particles having a particle size larger than 10 μm, which had an average particle size of 1.7 μm and which had the values $(R_C–R_A)$ and $(R_D–R_B)$ of 1.66 μm and 1.87 μm, respectively. The aforesaid toner composition was placed on a color copying machine available from the market (produced by Hitachi Ltd. under the trade name "HITACHI HT-4551-11") to proceed with picture image formation. As a result, there was obtained a vivid picture image with a high density free from surface contamination. Even after 20,000 sheets of picture image forming operation, a favorable cleaning condition was maintained without impairing the surface of the picture image support. Then the toner composition was left standing at 50° C. for 1 month, but no blocking of the toner composition was confirmed. Then picture image formation was performed by using the toner composition. As a result, as was the case with the picture image formation test before said standing, there was obtained a vivid picture image with a high density free from surface contamination.

COMPARATIVE EXAMPLES 6

The toner prepared in Preparation Examples 1 were placed on a monochromic copying machine available from the market (produced by CANON Inc. under the trade name "LBP404G") to proceed with picture image formation test for 20,000 sheets. After the formation of about 1000 sheets, filming was caused on the sheets, followed by surface contamination after about 5000 sheets, and practically unsuitable picture images with low image density were produced. As a result of observation for the surface of the picture image support after the completion of the running test, favorable cleaning conditions were not maintained.

COMPARATIVE EXAMPLES 7

To 100.0 parts by weight of the toner prepared in Preparation Example 1 was added 1 part by weight of zinc stearate which had particles having a particle size of 10 μm or larger of 10% by weight, which had an average particle size of 4.5 μm and which had the values $(R_C–R_A)$ and $(R_D–R_B)$ of 3.17 μm and 12.99 μm, respectively. The aforesaid toner composition was placed on a monochromic copying machine available from the market (produced by CANON Inc. under the trade name "LBP404G") to proceed with picture image formation test for 20,000 sheets. After the formation of about 15,000 sheets, surface contamination was caused on the sheets, and practically unsuitable picture images with low image density were produced. As a result of observation for the surface of the picture image support after the completion of the running test, the surface thereof was impaired and favorable cleaning conditions were not maintained.

COMPARATIVE EXAMPLES 8

To 100.0 parts by weight of the toner prepared in Preparation Example 1 was added 3 parts by weight of a mixture of calcium myristate and zinc behenate (1:1 by weight) which had particles having a particle size of 10 μm or larger of 12% by weight, which had an average particle size of 5.1 μm and which had the values $(R_C–R_A)$ and $(R_D–R_B)$ of 3.67 μm and 13.83 μm, respectively. The aforesaid toner composition was placed on a monochromic copying machine available from the market (produced by CANON Inc. under the trade name "LBP404G") to proceed with picture image formation test for 20,000 sheets. After the formation of about 12,000 sheets, surface contamination was caused on the sheets, and practically unsuitable picture images with low image density were produced. As a result of observation for the surface of the picture image support after the completion of the running test, the surface thereof was impaired and favorable cleaning conditions were not maintained.

COMPARATIVE EXAMPLES 9

To 100.0 parts by weight of the toner prepared in Preparation Example 1 was added 15 parts by weight of calcium stearate which had particles having a particle size of 10 μm in or larger of 61% by weight, which had an average particle size of 13.8 μm and which had the values $(R_C–R_A)$ and $(R_D–R_B)$ of 9.93 μm and 24.35 μm, respectively. The aforesaid toner composition was placed on a monochromic copying machine available from the market (produced by CANON Inc. under the trade name "LBP404G ")to proceed with picture image formation test for 20,000 sheets. After the formation of about 6,000 sheets, surface contamination was caused on the sheets, and practically unsuitable picture images with low image density were produced. As a result of observation for the surface of the picture image support after the completion of the running test, the surface thereof was impaired and favorable cleaning conditions were not maintained.

COMPARATIVE EXAMPLES 10

The toner prepared in Preparation Examples 2 were placed on a color copying machine available from the market (produced by Hitachi Ltd. under the trade name "HITACHI HT-4551-11") to proceed with picture image formation test for 20,000 sheets. After the formation of about 1000 sheets, filming was caused on the sheets, followed by surface contamination after about 6000 sheets, and practically unsuitable picture images with low image density were produced. As a result of observation for the surface of the picture image support after the completion of the running test, favorable cleaning conditions were not maintained. Said toner was allowed to stand at 60° C. for 2 weeks with a result that blocking occured on part of the toner.

COMPARATIVE EXAMPLES 11

To 100.0 parts by weight of the toner prepared in Preparation Example 2 was added 5 parts by weight of zinc stearate which had particles having a particle size of 10 μm or larger of 21% by weight, which had an average particle size of 73.5 μm and which had the values ($R_C$–$R_A$) and ($R_D$–$R_B$) of 5.52 μm and 15.36 μm, respectively. The aforesaid toner composition was placed on a color copying machine available from the market (produced by Hitachi Ltd. under the trade name "HITACHI HT-4551-11") to proceed with picture image formation test for 20,000 sheets. After the formation of about 8,000 sheets, filming was caused on the sheets, followed by surface contamination after about 11000 sheets, and practically unsuitable picture images with low image density were produced. As a result of observation for the surface of the picture image support after the completion of the running test, the surface thereof was impaired and favorable cleaning conditions were not maintained. Said toner composition was allowed to stand at 60° C. for 2 weeks with a result that blocking occured on part of the toner composition.

COMPARATIVE EXAMPLE 12

To 100.0 parts by weight of each of the color toners prepared in Preparation Example 2 was added one part by weight of a mixture of nickel stearate and zinc oleate (2:1 by weight) which had particles having a particle size of 10 μm or larger of 11% by weight, which had an average particle size of 5.3 μm and which had the values ($R_C$–$R_A$) and ($R_D$–$R_B$) of 3.51 μm and 13.01 μm, respectively. The aforesaid toner composition was placed on a color copying machine available from the market (produced by Hitachi Ltd. under the trade name "HITACHI HT-4551-11") to proceed with picture image formation test for 20,000 sheets. After the formation of about 7,500 sheets, filming was caused on the sheets, followed by surface contamination after about 9,500 sheets, and thus practically unsuitable picture images with low density were produced. As a result of observation for the surface of the picture image support after the completion of the running test, the surface thereof was impaired and further favorable cleaning conditions were not maintained. Said toner composition was allowed to stand at 60° C. for 2 weeks with a result that blocking occured on part of the toner composition.

COMPARATIVE EXAMPLE 13

To 100.0 parts by weight of each of the color toners prepared in Preparation Example 2 was added 0.5 part by weight of a mixture of barium stearate and calcium behenate (4:1 by weight) which had particles having a particle size of 10 μm or larger of 11% by weight, which had an average particle size of 8.5 μm and which had the values ($R_C$–$R_A$) and ($R_D$–$R_B$) of 6.12 μm and 18.41 μm, respectively. The aforesaid toner composition was placed on a color copying machine available from the market (produced by Hitachi Ltd. under the trade name "HITACHI HT-4551-11") to proceed with picture image formation test for 20,000 sheets. After the formation of about 5000 sheets, filming was caused on the sheets, followed by surface contamination after about 7000 sheets, and thus practically unsuitable picture images with low density were produced. As a result of observation for the surface of the picture image support after the completion of the running test, the surface thereof was impaired and further favorable cleaning conditions were not maintained. Said toner composition was allowed to stand at 60° C. for 2 weeks, with a result that blocking occured on part of the toner composition.

EXAMPLES 17 TO 22 AND COMPARATIVE EXAMPLES 14 TO 21

In the following, some description will be given of working examples and comparative examples in the case where metallic soap fine particles are used as a cleaning aid for an electronic copying machine. The picture image forming apparatus shown on the schematic drawing in FIG. 5 described in Japanese Patent Application Laid-Open No. 160165/1995 (Hei-7) was adopted as the apparatus to be used in the working examples and comparative examples.

EXAMPLE 17

Picture image formation test was carried out by the use of the unary non-magnetic developer described in Japanese Patent Application Laid-Open No. 127177/1992 (Hei-4) {hereinafter referred to as "toner A"}, while the surface of the rotating picture image support was coated from the region (a) by using a roll type brush, with the metallic soap fine particles as the cleaning aid comprising powdery zinc stearate which was free from particles having a particle size of 10 μm or larger, which had an average particle size of 1.3 μm and which had the values ($R_C$–$R_A$) and ($R_D$–$R_B$) of 1.51 μm and 2.21 μm, respectively. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

EXAMPLE 18

Picture image formation test was carried out by the use of said toner A, while the cleaning aid comprising the metallic soap fine particles consisting of a mixture of calcium myristate and calcium stearate (1:1 by weight) in the form of compressed plate was fixed so as to frictionally slide on the surface of the rotating picture-image support from the region (d); said mixture being free from particles having a particle size of 10 μm or larger, having an average particle size of 1.8 μm and having the values ($R_C$–$R_A$) and ($R_D$–$R_B$) of 1.73 μm and 2.38 μm, respectively. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

EXAMPLE 19

Picture image formation test was carried out by the use of said toner A, while the cleaning aid comprising the metallic soap fine particles consisting of a mixture of calcium octanoate and calcium stearate (1:10 by weight) in the form of compressed plate was fixed so as to frictionally slide on the surface of the rotating picture-image support from the region (d); said mixture being free from particles having a particle size of 10 μm or larger, said mixture having an average particle size of 2.1 μm and having the values ($R_C$–$R_A$) and ($R_D$–$R_B$) of 1.52 μm and 2.19 μm, respectively. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

EXAMPLE 20

Picture image formation test was carried out by the use of said toner A, while the surface of an electrification roll 8 was coated in a thickness of 200 μm, with the cleaning aid comprising the metallic soap fine particles consisting of a mixture of barium laurate and zinc stearate (1:5 by weight), and the surface of the rotating picture-image support was coated with said cleaning aid from said electrification roll 8, said mixture being free from particles having a particle size of 10 μm or larger, said mixture having an average particle size of 0.8 μm and having the values $(R_C-R_A)$ and $(R_D-R_B)$ of 0.45 m and 2.51 μm, respectively. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

EXAMPLE 21

A cleaning aid was prepared by blending a mixture which was composed of magnesium palmitate and calcium behenate (1:3 by weight), which had particles having a particle size of 10 μm or larger of 1% by weight, which had an average particle size of 1.7 μm and which had the values $(R_C-R_A)$ and $(R_D-R_B)$ of 1.66 μm and 1.87 μm, respectively; polytetrafluoroethylene resin; and alumina in a ratio by weight of 6:2:1. Subsequently, picture image formation test was carried out by the use of a dispersion polymerization type developer with an average particle size of 6 μm described in Japanese Patent Application Laid-Open No. 137372/1992 (Hei-4) {hereinafter referred to as "toner B"}, while the surface of a cleaning blade 12 was coated in a thickness of 300 μm, with the above-prepared cleaning aid, and the surface of the rotating picture-image support was coated with said cleaning aid from said cleaning blade 12. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

EXAMPLE 22

A cleaning aid was prepared by blending zinc behenate which had particles having a particle size of 10 μm or larger of 1% by weight, which had an average particle size of 2.3 μm and which had the values $(R_C-R_A)$ and $(R_D-R_B)$ of 1.80 μm and 2.31 μm, respectively; silica; and teflon in a ratio by weight of 3:1:1. Subsequently, picture image formation test was carried out by the use of said toner B, while the surface of the rotating picture-image support was coated from the region (a) by using a sponge roll, with said cleaning aid. As a result, there was obtained a vivid picture image with a high density free from surface contamination. The picture image formation running test was further carried out for 20,000 sheets. As a result, there were obtained vivid picture images with a high density free from surface contamination even at the last 20,000th sheet. As a result of observation for the surface conditions of the picture image support after the completion of the running test, there were maintained favorable surface conditions thereof and further favorable cleaning conditions thereon.

COMPARATIVE EXAMPLE 14

Picture image formation running test was carried out for 20,000 sheets by the use of the picture image forming apparatus as shown in FIG. 6 and of the toner A without using any cleaning aid according to the present invention. As a result, after the formation of about 1,000 sheets, filming was caused on the sheets, followed by surface contamination after about 2000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 15

Picture image formation test was carried out for 20,000 sheets by the use of said toner A, while the surface of the rotating picture-image support was coated from the region (a) by using a roll type brush, with powdery zinc stearate which had particles having a particle size of 10 μm or larger of 10% by weight, which had an average particle size of 4.5 μm and which had the values $(R_C-R_A)$ and $(R_D-R_B)$ of 3.17 μm and 12.99 μm, respectively. As a result, after the formation of about 15,000 sheets, filming was caused on the sheets, followed by surface contamination after about 17,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 16

Picture image formation test was carried out for 20,000 sheets by the use of said toner A, while a mixture of calcium myristate and zinc behenate (1:1 by weight) in the form of compressed plate was fixed so as to frictionally slide on the surface of the rotating picture-image support from the region (d), said mixture having particles with a particle size of 10 μm or larger of 12% by weight, having an average particle size of 5.1 μm and having the values $(R^C-R_A)$ and $(R_D-R_B)$ of 3.67 μm and 13.83 μm, respectively. As a result, after the formation of about 12,000 sheets, filming was caused on the sheets, followed by surface contamination after about 15,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 17

Picture image formation test was carried out for 20,000 sheets by the use of said toner A, while a mixture of calcium stearate and zinc oleate (3:1 by weight) in the form of compressed plate was fixed so as to frictionally slide on the surface of the rotating picture-image support from the region (d), said mixture having particles with a particle size of 10 μm or larger of 61% by weight, having an average particle size of 13.8 μm and having the values ($R_C$–$R_A$) and ($R_D$–$R_B$) of 9.93 μm and 24.35 μm, respectively. As a result, after the formation of about 15,000 sheets, filming was caused on the sheets, followed by surface contamination after about 17,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 18

Picture image formation test was carried out for 20,000 sheets by the use of said toner A, while the surface of an electrification roll 8 was coated in a thickness of 300 μm, with a cleaning aid consisting of a mixture of calcium butanoate and zinc oleate (1:6 by weight), and the surface of the rotating picture-image support was coated with said cleaning aid from said electrification roll 8, said mixture having particles with a particle size of 10 μm or larger of 21% by weight, having an average particle size of 7.5 μm and having the values ($R_C$–$R_A$) and ($R_D$–$R_B$) of 5.52 μm and 15.36 μm, respectively. As a result, after the formation of about 10,000 sheets, filming was caused on the sheets, followed by surface contamination after about 12,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 19

A cleaning aid was prepared by blending calcium stearate which had particles having a particle size of 10 μm or larger of 11% by weight, which had an average particle size of 5.3 μm and which had the values ($R_C$–$R_A$) and ($R_D$–$R_B$) of 3.51 μm and 13.01 μm, respectively; and alumina in a ratio by weight of 6:1. Subsequently, picture image formation test was carried out for 20,000 sheets by the use of said toner B, while the surface of a cleaning blade 12 was coated in a thickness of 100 μm, with the above-prepared cleaning aid, and the surface of the rotating picture-image support was coated with said cleaning aid from said cleaning blade 12. As a result, after the formation of about 7,000 sheets, filming was caused on the sheets, followed by surface contamination after about 10,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 20

A cleaning aid was prepared by blending zinc stearate which had particles having a particle size of 10 μm or larger of 27% by weight, which had an average particle size of 8.5 μm and which had the values ($R_C$–$R_A$) and ($R_D$–$R_B$) of 6.12 μm and 18.41 μm, respectively; and teflon in a ratio by weight of 3:1. Subsequently, picture image formation test was carried out for 20,000 sheets by the use of said toner B, while the surface of the rotating picture-image support was coated with said cleaning aid from the region (a) by using a sponge roll. As a result, after the formation of about 7,000 sheets, filming was caused on the sheets, followed by surface contamination after about 9,000 sheets, and thus practically unsuitable picture images with low density were produced. As a result of observation for the surface of the picture image support after the completion of the running test, the surface thereof was impaired and further favorable cleaning conditions were not maintained.

COMPARATIVE EXAMPLE 21

There was prepared a mixture which was composed of nickel stearate and zinc oleate (2:1 by weight), which had particles with a particle size of 10 μm or larger of 12% by weight, which had an average particle size of 4.9 μm and which had the values ($R_C$–$R_A$) and ($R_D$–$R_B$) of 3.31 μm and 13.51 μm, respectively. Subsequently, picture image formation test was carried out for 20,000 sheets, while 0.7 part by weight of the mixture thus prepared was externally added to said toner B, and the resultant composition (mixture/toner B) was applied as coating onto the surface of the rotating picture-image support from a developing apparatus 3. As a result, after the formation of about 6,500 sheets, filming was caused on the sheets, followed by surface contamination after about 9,000 sheets, and thus practically unsuitable picture images with low density were produced. As a result of observation for the surface of the picture image support after the completion of the running test, the surface thereof was impaired and further favorable cleaning conditions were not maintained.

TABLE 1

| | | |
|---|---|---|
| Starting Material | 1-(1) | potassium palmitate |
| | 1-(2) | sodium stearate |
| | 1-(3) | ammonium stearate |
| | 1-(4) | sodium behenate |
| | 1-(5) | sodium oleate |
| | 1-(6) | ammonium salt of beef tallow fatty acid |
| | 1-(7) | sodium laurate |
| | 1-(8) | stearic acid |
| Starting Material | 2-(1) | zinc sulfate |
| | 2-(2) | calcium chloride |
| | 2-(3) | magnesium sulfate |
| | 2-(4) | copper sulfate |
| | 2-(5) | barium nitrate |
| | 2-(6) | nickel chloride |
| | 2-(7) | calcium hydroxide |

TABLE 2

| | Component (a) | | | Component (b) | | | Mixing Condition | | | Dry Condition | | |
|---|---|---|---|---|---|---|---|---|---|---|---|---|
| | Start Mat. 1 | Temp °C. | Conc wt % | Start Mat. 2 | Temp °C. | Conc wt % | Mixing Method | Equivalent Ratio, a/b | Cleaning Solvent for M.S. after cleaning | Temp °C. | Press | S.T.C.T. °C. |
| Ex. 1 | 1-(1) | 80 | 1 | 2-(2) | 80 | 0.5 | A | 0.90 | water | 70 | atm | 73 |
| Ex. 2 | 1-(2) | 85 | 0.5 | 2-(1) | 85 | 0.2 | A | 1.00 | methanol | 90 | atm | 100 |
| Ex. 3 | 1-(2) | 85 | 5 | 2-(1) | 85 | 3 | B | 0.95 | $CH_2Cl_2$ | 80 | atm | 100 |
| Ex. 4 | 1-(2) | 85 | 10 | 2-(1) | 85 | 3 | B | 1.05 | water | 50 | atm | 100 |
| Ex. 5 | 1-(3) | 75 | 2 | 2-(5) | 75 | 0.5 | A | 0.95 | acetone | 70 | atm | 145 |
| Ex. 6 | 1-(4) | 75 | 10 | 2-(4) | 75 | 3 | A | 0.98 | $CH_2Cl_2$ | 60 | atm | 106 |
| Ex. 7 | 1-(5) | 80 | 2 | 2-(6) | 80 | 1 | B | 0.95 | water | 80 | atm | 89 |
| Ex. 8 | 1-(6) | 80 | 12 | 2-(1) | 80 | 7 | B | 1.10 | water | 80 | atm | 103 |
| Ex. 9 | 1-(1) | 80 | 0.005 | 2-(1) | 80 | 0.005 | A | 0.98 | water | 90 | atm | 100 |
| Ex. 10 | 1-(2) | 80 | 14 | 2-(1) | 80 | 8 | A | 1.02 | ethanol/water | 80 | atm | 100 |
| Ex. 11 | 1-(7) | 70 | 0.03 | 2-(3) | 70 | 0.01 | B | 0.95 | water | 65 | vac | 73 |
| CEx. 1 | 1-(2) | 80 | 5 | 2-(1) | 80 | 2 | B | 0.98 | water | 110 | atm | 100 |
| CEx. 2 | 1-(2) | 80 | 30 | 2-(1) | 80 | 25 | A | 0.98 | water | 80 | atm | 100 |
| CEx. 3 | 1-(5) | 80 | 5 | 2-(3) | 80 | 3 | B | 1.40 | methanol | 80 | atm | 73 |
| CEx. 4 | 1-(2) | 80 | 15 | 2-(1) | 80 | 25 | DD | 0.98 | water | 110 | atm | 100 |
| CEx. 5 | 1-(8) | 70 | — | 2-(7) | 20 | — | Fusion | — | No cleaning | — | — | 94 |

[Renarks]
Ex.: Example,
CEx.: Comparative Example,
Start Mat: starting material,
M.S.: metallic soap,
Press: pressure,
atm: atmospheric pressure,
vac: reduced pressure,
S.T.C.T.: starting temperature for crystal transition,
$CH_2Cl_2$: methylene chloride (dichloromethane),
DD: double decomposition.

TABLE 3

| | Content of M.S. in slurry wt % | Yield g | M.S. Yield % | Average particle size µm | Particle size (µm) showing cumulative content in (%) | | | | $R_C - R_A$ (µ) | $R_D - R_B$ (µ) | Content of particles >10µ (%) |
|---|---|---|---|---|---|---|---|---|---|---|---|
| | | | | | 30% $R_A$ | 50% $R_B$ | 70% $R_C$ | 95% $R_D$ | | | |
| Ex. 1 | 2.01 | 10.0 | 99 | 1.3 | 0.79 | 1.32 | 2.30 | 3.53 | 1.51 | 2.21 | 0 |
| Ex. 2 | 0.31 | 1.6 | 100 | 0.8 | 0.50 | 0.69 | 0.95 | 3.20 | 0.45 | 2.51 | 0 |
| Ex. 3 | 3.53 | 17.6 | 100 | 1.4 | 0.82 | 1.48 | 2.44 | 3.64 | 1.62 | 2.16 | 0 |
| Ex. 4 | 5.62 | 28.1 | 100 | 1.8 | 1.04 | 1.91 | 2.77 | 4.28 | 1.73 | 2.38 | 0 |
| Ex. 5 | 0.97 | 4.8 | 99 | 1.7 | 1.00 | 1.82 | 2.66 | 3.70 | 1.66 | 1.87 | 0 |
| Ex. 6 | 5.99 | 29.9 | 99 | 2.0 | 1.41 | 2.16 | 2.91 | 4.43 | 1.50 | 2.18 | 0 |
| Ex. 7 | 1.30 | 6.5 | 98 | 1.8 | 1.07 | 1.92 | 2.76 | 4.19 | 1.69 | 2.27 | 0 |
| Ex. 8 | 8.79 | 44.0 | 99 | 2.1 | 1.45 | 2.20 | 2.96 | 4.47 | 1.51 | 2.27 | 0 |
| Ex. 9 | 0.004 | 0.02 | 98 | 0.6 | 0.47 | 0.62 | 0.85 | 2.95 | 0.38 | 2.33 | 0 |
| Ex. 10 | 10.74 | 53.2 | 99 | 3.1 | 1.75 | 3.00 | 3.24 | 8.82 | 1.49 | 5.82 | 0 |
| Ex. 11 | 0.01 | 0.047 | 98 | 1.2 | 0.73 | 1.30 | 2.25 | 3.32 | 1.52 | 2.02 | 0 |
| CEx. 1 | 3.53 | 17.6 | 100 | 4.2 | 2.10 | 3.73 | 5.67 | 9.90 | 3.53 | 6.17 | 5 |
| CEx. 2 | 23.30 | 115.8 | 100 | 5.1 | 2.44 | 3.98 | 6.11 | 17.81 | 3.67 | 13.83 | 12 |
| CEx. 3 | 3.86 | 19.3 | 99 | 4.5 | 1.87 | 3.13 | 5.04 | 6.12 | 3.17 | 12.99 | 10 |
| CEx. 4 | 13.32 | 66.6 | 100 | 7.5 | 3.24 | 5.26 | 8.76 | 20.62 | 5.52 | 15.36 | 21 |
| CEx. 5 | — | 580 | 90 | 13.5 | 8.19 | 12.45 | 18.12 | 36.80 | 9.93 | 24.35 | 61 |

| Cumulation of Amount of Metallic Soap Fine Particles (%) | | | | | | | |
|---|---|---|---|---|---|---|---|
| | 0.34 µm | 0.66 µm | 1.01 µm | 3.73 µm | 5.27 µm | 10.55 µm | 21.10 µm | 42.21 µm |
| Ex. 1 | 3.3 | 22.0 | 43.7 | 99.0 | 100.0 | 100.0 | 100.0 | 100.0 |
| Ex. 2 | 11.5 | 48.0 | 74.5 | 100.0 | 100.0 | 100.0 | 100.0 | 100.0 |
| Ex. 3 | 4.0 | 21.2 | 40.2 | 96.9 | 100.0 | 100.0 | 100.0 | 100.0 |
| Ex. 4 | 2.6 | 14.7 | 29.3 | 92.2 | 100.0 | 100.0 | 100.0 | 100.0 |
| Ex. 5 | 2.7 | 15.3 | 30.5 | 95.8 | 100.0 | 100.0 | 100.0 | 100.0 |
| Ex. 6 | 2.4 | 8.6 | 19.4 | 91.7 | 100.0 | 100.0 | 100.0 | 100.0 |
| Ex. 7 | 2.0 | 14.1 | 28.5 | 92.7 | 100.0 | 100.0 | 100.0 | 100.0 |
| Ex. 8 | 2.1 | 8.1 | 18.5 | 90.4 | 100.0 | 100.0 | 100.0 | 100.0 |
| Ex. 9 | 12.3 | 65.9 | 82.5 | 100.0 | 100.0 | 100.0 | 100.0 | 100.0 |

TABLE 3-continued

| | | | | | | | |
|---|---|---|---|---|---|---|---|
| Ex. 10 | 1.9 | 8.5 | 17.2 | 54.3 | 78.1 | 100.0 | 100.0 | 100.0 |
| Ex. 11 | 3.4 | 22.5 | 45.8 | 99.5 | 100.0 | 100.0 | 100.0 | 100.0 |
| CEx. 1 | 2.1 | 0.3 | 16.6 | 50.0 | 67.9 | 98.8 | 100.0 | 100.0 |
| CEx. 2 | 1.2 | 5.5 | 11.4 | 46.8 | 66.5 | 88.6 | 97.9 | 100.0 |
| CEx. 3 | 1.1 | 7.9 | 16.3 | 59.6 | 71.8 | 90.3 | 99.2 | 100.0 |
| CEx. 4 | 0.5 | 2.3 | 5.2 | 35.5 | 50.1 | 80.2 | 95.7 | 100.0 |
| CEx. 5 | 0.0 | 0.0 | 0.0 | 5.4 | 13.5 | 43.3 | 80.5 | 100.0 |

[Remarks]
Ex.: Example,
CEx.: Comparative Example,
All % is based on weight unless otherwise specified
M.S.: metallic soap

What is claimed is:

1. Metallic soap fine particles, comprising metallic soap particles which have an average particle size of 4 μm or smaller and have a content of particles having particle sizes of 10 μm or larger of at most 4% by weight based on the whole metallic soap particles, said particle size being measured at the time of particle production or after drying but prior to any other post-treatment.

2. The metallic soap fine particles according to claim 1, Go wherein said particles have an average particle size in the range of 0.5 to 2.5 μm, have a content of particles having particle sizes of 6 μm or larger of at most 5% by weight based on the whole metallic soap particles, and are substantially free from particles having particle sizes of 10 μm or larger.

3. The metallic soap fine particles according to claim 1 or 2, wherein the difference in particle size ($R_C$–$R_A$) is at most 3 μm between the particle size showing 70% ($R_C$) in a cumulative particle size distribution curve for said metallic soap fine particles and the particle size showing 30% ($R_A$) in the same.

4. The metallic soap fine particles according to claim 3, wherein the difference in particle size ($R_C$–$R_A$) is in the range of 0.3 to 2 μm between the particle size showing 70% ($R_C$) in said curve and the particle size showing 30% ($R_A$) in the same.

5. The metallic soap fine particles according to claim 1 or 2, wherein the difference in particle size ($R_D$–$R_B$) is at most 6 μm between the particle size showing 95% ($R_D$) in a cumulative particle size distribution curve for said metallic soap fine particles and the particle size showing 50% ($R_B$) in the same.

6. The metallic soap fine particles according to claim 5, wherein the difference in particle size ($R_D$–$R_B$) is in the range of 1.5 to 6 μm between the particle size showing 95% ($R_D$) in said curve and the particle size showing 50% ($R_D$) in the same.

7. The metallic soap fine particles according to claim 1, wherein said particles are produced at a temperature not higher than the starting temperature for crystal transition of the metallic soap.

8. The metallic soap fine particles according to claim 7, wherein said particles are produced at a temperature lower than the starting temperature for crystal transition of the metallic soap by at least 5° C.

9. A process for producing the metallic soap fine particles as set forth in any one of claims 1, 2, 7 and 8 which comprises the steps of mixing (a) an aqueous solution containing 0.001 to 20% by weight of an alkali metal salt or an ammonium salt of a fatty acid having 4 to 30 carbon atoms with (b) an aqueous solution or dispersion containing 0.001 to 20% by weight of an inorganic metal salt at a temperature not higher than the starting temperature for crystal transition of metallic soap to be produced so as to form a slurry of the metallic soap; and drying treating the resultant slurry at a temperature not higher than the starting temperature for crystal transition of the metallic soap.

10. The process for producing the metallic soap fine particles according to claim 9 which comprises the steps of mixing (a) an aqueous solution containing 0.5 to 15% by weight of an alkali metal salt or an ammonium salt of a fatty acid having 12 to 22 carbon atoms with (b) an aqueous solution or dispersion containing 0.01 to 10% by weight of an inorganic metal salt at a temperature lower than the starting temperature for crystal transition of metallic soap to be produced by at least 5° C. so as to form a slurry of the metallic soap; and drying-treating the resultant slurry at a temperature lower than the starting temperature for crystal transition of the metallic soap by at least 5° C.

11. A toner composition for an electrophotographic copying machine which comprises a toner and the metallic soap fine particles as set forth in any one of claims 1, 2, 7 and 8.

12. The toner composition for an electrophotographic copying machine according to claim 11, wherein the content of the metallic soap fine particles is in the range of 0.05 to 50% by weight based on a resin for said toner.

13. A cleaning aid for an electrophotographic copying machine which comprises the metallic soap fine particles as set forth in any one of claims 1, 2, 7 and 8.

* * * * *